US008831730B2

(12) United States Patent
Mashiach et al.

(10) Patent No.: US 8,831,730 B2
(45) Date of Patent: Sep. 9, 2014

(54) SELF RESONANT TRANSMITTING DEVICE

(71) Applicants: Adi Mashiach, Tel Aviv (IL); Carsten Mueller, Ensheimer Strasse (DE)

(72) Inventors: Adi Mashiach, Tel Aviv (IL); Carsten Mueller, Ensheimer Strasse (DE)

(73) Assignee: Nyxoah SA, Mont-St-Guibert (BE)

( * ) Notice: Subject to any disclaimer, the term of this patent is extended or adjusted under 35 U.S.C. 154(b) by 0 days.

(21) Appl. No.: 14/059,643

(22) Filed: Oct. 22, 2013

(65) Prior Publication Data
US 2014/0052212 A1    Feb. 20, 2014

Related U.S. Application Data

(63) Continuation of application No. 13/952,015, filed on Jul. 26, 2013.

(60) Provisional application No. 61/676,327, filed on Jul. 26, 2012.

(51) Int. Cl.
A61N 1/05    (2006.01)
A61N 1/36    (2006.01)
A61N 1/372   (2006.01)
A61N 1/378   (2006.01)

(52) U.S. Cl.
CPC .......... A61N 1/3606 (2013.01); A61N 1/37229 (2013.01); A61N 1/3787 (2013.01)
USPC ........................................................ 607/42

(58) Field of Classification Search
CPC . A61N 1/3601; A61N 1/3611; A61N 1/3787; A61N 1/0551; A61N 1/0558; A61N 1/0553; A61N 1/3605; A61N 1/3606; A61N 1/37229; A61B 5/4818; A61B 5/0031
USPC ................... 607/42, 62, 46, 116, 44
See application file for complete search history.

(56) References Cited

U.S. PATENT DOCUMENTS

| 5,690,693 | A  | 11/1997 | Wang |
| 7,016,738 | B1 | 3/2006  | Karunasiri |
| 7,177,691 | B2 | 2/2007  | Meadows et al. |
| 7,225,032 | B2 | 5/2007  | Schmeling et al. |
| 7,286,880 | B2 | 10/2007 | Olson et al. |

(Continued)

FOREIGN PATENT DOCUMENTS

WO    WO 2007/118194    10/2007

OTHER PUBLICATIONS

PCT Search Report and Written Opinion for International Application No. PCT/IB13/2127, dated May 16, 2014; 5 pgs.

Primary Examiner — Rex R Holmes
(74) Attorney, Agent, or Firm — Finnegan, Henderson, Farabow, Garrett & Dunner, LLP

(57) ABSTRACT

A device for powering an implant within a body of a subject from a location external to the subject, wherein the implant requires a threshold rate of power increase in order to operate in at least one mode, may include an antenna configured to wirelessly transmit energy to the implant. The device may also include a power storage unit configured to store energy from a power source incapable of delivering the threshold rate of power increase to enable the implant unit to operate in the at least one mode and a power release unit configured to release a pulse of energy from the power storage unit to the antenna after the power storage unit collects an amount of energy sufficient to enable the implant unit to operate in the at least one mode.

8 Claims, 11 Drawing Sheets

(56) References Cited

U.S. PATENT DOCUMENTS

| | | |
|---|---|---|
| 7,286,881 B2 | 10/2007 | Schommer et al. |
| 7,513,896 B2 | 4/2009 | Orszulak |
| 7,515,967 B2 | 4/2009 | Phillips et al. |
| 7,648,499 B2 | 1/2010 | Orszulak et al. |
| 8,140,168 B2 | 3/2012 | Olson et al. |
| 8,165,678 B2 | 4/2012 | Forsberg et al. |
| 8,175,717 B2 | 5/2012 | Haller et al. |
| 8,265,770 B2 | 9/2012 | Toy et al. |
| 2002/0188333 A1 | 12/2002 | Nowick et al. |
| 2005/0288739 A1 | 12/2005 | Hassler et al. |
| 2005/0288743 A1 | 12/2005 | Ahn |
| 2007/0233204 A1* | 10/2007 | Lima et al. ............ 607/46 |
| 2009/0105782 A1 | 4/2009 | Mickle et al. |
| 2009/0210035 A1 | 8/2009 | Galbart et al. |
| 2010/0114252 A1 | 5/2010 | Torgerson |
| 2011/0009924 A1 | 1/2011 | Meskens |
| 2011/0213438 A1 | 9/2011 | Lima |
| 2011/0301669 A1 | 12/2011 | Olson |
| 2011/0307034 A1 | 12/2011 | Hastings et al. |
| 2012/0153735 A1 | 6/2012 | Karalis et al. |
| 2012/0172948 A1 | 7/2012 | Aghassian |
| 2012/0235502 A1 | 9/2012 | Kesler et al. |
| 2012/0235503 A1 | 9/2012 | Kesler et al. |
| 2012/0235633 A1 | 9/2012 | Kesler et al. |
| 2012/0262108 A1 | 10/2012 | Olson et al. |
| 2013/0310901 A1* | 11/2013 | Perryman et al. ............ 607/72 |

* cited by examiner

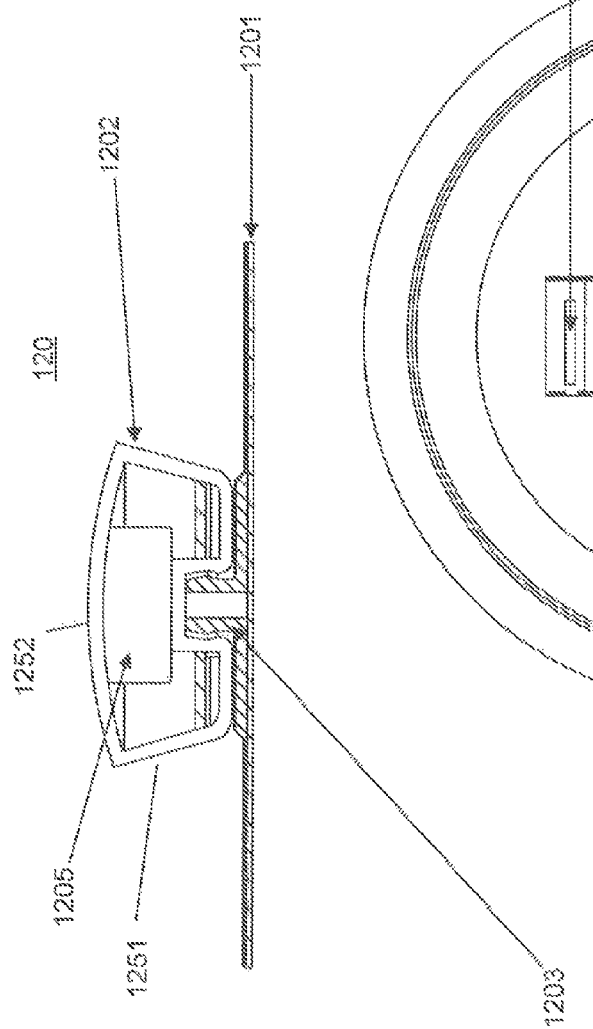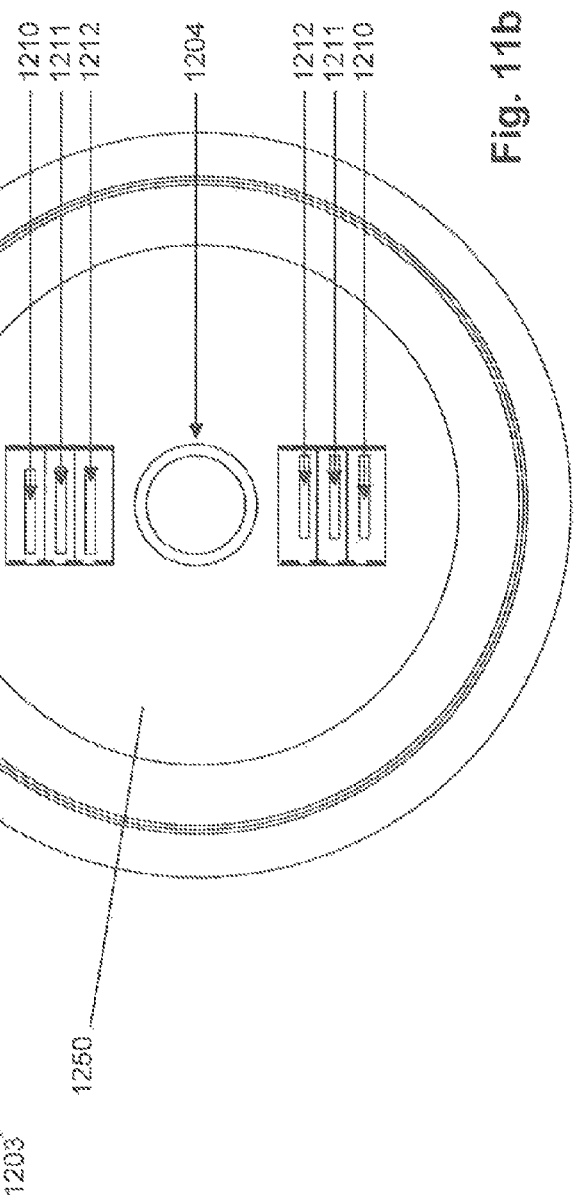

SELF RESONANT TRANSMITTING DEVICE

RELATED APPLICATIONS

This application is a continuation of application Ser. No. 13/952,015, filed on Jul. 26, 2013, which claims the benefit of priority under 35 U.S.C. §119(e) to U.S. Provisional Application No. 61/676,327, filed Jul. 26, 2012, each of which are incorporated herein by reference.

TECHNICAL FIELD

Embodiments of the present disclosure generally relate to devices and methods for conveying power from a location external to a subject to a location within the subject. More particularly, embodiments of the present disclosure relate to devices and methods for transcutaneously conveying power to an implanted neuromodulation device.

BACKGROUND

Neural modulation presents the opportunity to treat many physiological conditions and disorders by interacting with the body's own natural neural processes. Neural modulation includes inhibition (e.g. blockage), stimulation, modification, regulation, or therapeutic alteration of activity, electrical or chemical, in the central, peripheral, or autonomic nervous system. By modulating the activity of the nervous system, for example through the stimulation of nerves or the blockage of nerve signals, several different goals may be achieved. Motor neurons may be stimulated at appropriate times to cause muscle contractions. Sensory neurons may be blocked, for instance to relieve pain, or stimulated, for instance to provide a signal to a subject. In other examples, modulation of the autonomic nervous system may be used to adjust various involuntary physiological parameters, such as heart rate and blood pressure. Neural modulation may provide the opportunity to treat several diseases or physiological conditions, a few examples of which are described in detail below.

Among the conditions to which neural modulation may be applied is sleep disordered breathing, examples of which include obstructive sleep apnea (OSA) and snoring. OSA is a respiratory disorder characterized by recurrent episodes of partial or complete obstruction of the upper airway during sleep. During the sleep of a person without OSA, the pharyngeal muscles relax during sleep and gradually collapse, narrowing the airway. The airway narrowing limits the effectiveness of the sleeper's breathing, causing a rise in $CO_2$ levels in the blood. The increase in $CO_2$ results in the pharyngeal muscles contracting to open the airway to restore proper breathing. The largest of the pharyngeal muscles responsible for upper airway dilation is the genioglossus muscle, which is one of several different muscles in the tongue. The genioglossus muscle is responsible for forward tongue movement and the stiffening of the anterior pharyngeal wall. In patients with OSA, the neuromuscular activity of the genioglossus muscle is decreased compared to normal individuals, accounting for insufficient response and contraction to open the airway as compared to a normal individual. This lack of response contributes to a partial or total airway obstruction, which significantly limits the effectiveness of the sleeper's breathing. In OSA patients, there are often several airway obstruction events during the night. Because of the obstruction, there is a gradual decrease of oxygen levels in the blood (hypoxemia). Hypoxemia leads to night time arousals, which may be registered by EEG, showing that the brain awakes from any stage of sleep to a short arousal. During the arousal, there is a conscious breath or gasp, which resolves the airway obstruction. An increase in sympathetic tone activity rate through the release of hormones such as epinephrine and noradrenaline also often occurs as a response to hypoxemia. As a result of the increase in sympathetic tone, the heart enlarges in an attempt to pump more blood and increase the blood pressure and heart rate, further arousing the patient. After the resolution of the apnea event, as the patient returns to sleep, the airway collapses again, leading to further arousals.

These repeated arousals, combined with repeated hypoxemia, leaves the patient sleep deprived, which leads to daytime somnolence and worsens cognitive function. This cycle can repeat itself up to hundreds of times per night in severe patients. Thus, the repeated fluctuations in and sympathetic tone and episodes of elevated blood pressure during the night evolve to high blood pressure through the entire day. Subsequently, high blood pressure and increased heart rate may cause other diseases.

Efforts for treating OSA include Continuous Positive Airway Pressure (CPAP) treatment, which requires the patient to wear a mask through which air is blown into the nostrils to keep the airway open. Other treatment options include the implantation of rigid inserts in the soft palate to provide structural support, tracheotomies, or tissue ablation.

Another condition to which neural modulation may be applied is the occurrence of migraine headaches. Pain sensation in the head is transmitted to the brain via the occipital nerve, specifically the greater occipital nerve, and the trigeminal nerve. When a subject experiences head pain, such as during a migraine headache, the inhibition of these nerves may serve to decrease or eliminate the sensation of pain.

Neural modulation may also be applied to hypertension. Blood pressure in the body is controlled via multiple feedback mechanisms. For example, baroreceptors in the carotid body in the carotid artery are sensitive to blood pressure changes within the carotid artery. The baroreceptors generate signals that are conducted to the brain via the glossopharyngeal nerve when blood pressure rises, signaling the brain to activate the body's regulation system to lower blood pressure, e.g. through changes to heart rate, and vasodilation/vasoconstriction. Conversely, parasympathetic nerve fibers on and around the renal arteries generate signals that are carried to the kidneys to initiate actions, such as salt retention and the release of angiotensin, which raise blood pressure. Modulating these nerves may provide the ability to exert some external control over blood pressure.

The foregoing are just a few examples of conditions to which neuromodulation may be of benefit, however embodiments of the invention described hereafter are not necessarily limited to treating only the above-described conditions.

SUMMARY

A device according to some embodiments of the disclosure may be configured for powering an implant within a body of a subject from a location external to the subject, wherein the implant requires a threshold rate of power increase in order to operate in at least one mode. Such a device may include an antenna configured to wirelessly transmit energy to the implant, a power storage unit configured to store energy from a power source incapable of delivering the threshold rate of power increase to enable the implant unit to operate in the at least one mode, and a power release unit configured to release a pulse of energy from the power storage unit to the antenna after the power storage unit collects an amount of energy sufficient to enable the implant unit to operate in the at least one mode.

In another embodiment, a device for transmitting power from a location external to a body of a subject to an implant unit internal to the body of the subject may be provided. The device may include an external circuit including an antenna and having a resonant frequency that varies temporally based on, e.g., environmental conditions, and a processor configured to cause delivery of an impulse of energy to the external circuit to excite the external circuit and cause oscillations in the external circuit at a current resonant frequency of the external circuit such that power is delivered from the antenna to the implant unit at the current resonant frequency of the external circuit In still another embodiment, a device for transmitting power from a location external to a body of a subject to an implant unit internal to the body of the subject is provided. The device may include an antenna configured to be located external to a subject, a power source, a power storage unit, a power release unit, and at least one processor configured to control the power release unit. In the device, at least the antenna may be part of an external circuit having a resonance frequency. Furthermore, the power release unit may be configured such that, when in an open position, the power storage unit receives power from the primary power source and, when in a closed position, the power release unit releases power to the primary antenna, generating an oscillation in the primary antenna at the resonance frequency.

Additional features of the disclosure will be set forth in part in the description that follows, and in part will be obvious from the description, or may be learned by practice of the disclosed embodiments.

It is to be understood that both the foregoing general description and the following detailed description are exemplary and explanatory only, and are not restrictive of the invention, as claimed.

BRIEF DESCRIPTION OF THE DRAWINGS

The accompanying drawings, which are incorporated in and constitute a part of this specification, illustrate several embodiments of the disclosure and, together with the description, serve to explain the principles of the embodiments disclosed herein.

FIGS. 11a and 11b illustrate an exemplary embodiment of an external unit.

DESCRIPTION OF EXEMPLARY EMBODIMENTS

Reference will now be made in detail to exemplary embodiments of the present disclosure, examples of which are illustrated in the accompanying drawings. Wherever possible, the same reference numbers will be used throughout the drawings to refer to the same or like parts.

Embodiments of the present disclosure relate generally to a device for modulating a nerve through the delivery of energy. Nerve modulation, or neural modulation, includes inhibition (e.g. blockage), stimulation, modification, regulation, or therapeutic alteration of activity, electrical or chemical, in the central, peripheral, or autonomic nervous system. Nerve modulation may take the form of nerve stimulation, which may include providing energy to the nerve to create a voltage change sufficient for the nerve to activate, or propagate an electrical signal of its own. Nerve modulation may also take the form of nerve inhibition, which may including providing energy to the nerve sufficient to prevent the nerve from propagating electrical signals. Nerve inhibition may be performed through the constant application of energy, and may also be performed through the application of enough energy to inhibit the function of the nerve for some time after the application. Other forms of neural modulation may modify the function of a nerve, causing a heightened or lessened degree of sensitivity. As referred to herein, modulation of a nerve may include modulation of an entire nerve and/or modulation of a portion of a nerve. For example, modulation of a motor neuron may be performed to affect only those portions of the neuron that are distal of the location to which energy is applied.

In patients with OSA, for example, a primary target response of nerve stimulation may include contraction of a tongue muscle (e.g., the muscle) in order to move the tongue to a position that does not block the patient's airway. In the treatment of migraine headaches, nerve inhibition may be used to reduce or eliminate the sensation of pain. In the treatment of hypertension, neural modulation may be used to increase, decrease, eliminate or otherwise modify nerve signals generated by the body to regulate blood pressure.

While embodiments of the present disclosure may be disclosed for use in patients with specific conditions, the embodiments may be used in conjunction with any patient/portion of a body where nerve modulation may be desired. That is, in addition to use in patients with OSA, migraine headaches, or hypertension, embodiments of the present disclosure may be use in many other areas, including, but not limited to: deep brain stimulation (e.g., treatment of epilepsy, Parkinson's, and depression); cardiac pace-making, stomach muscle stimulation (e.g., treatment of obesity), back pain, incontinence, menstrual pain, and/or any other condition that may be affected by neural modulation.

Figure 1:
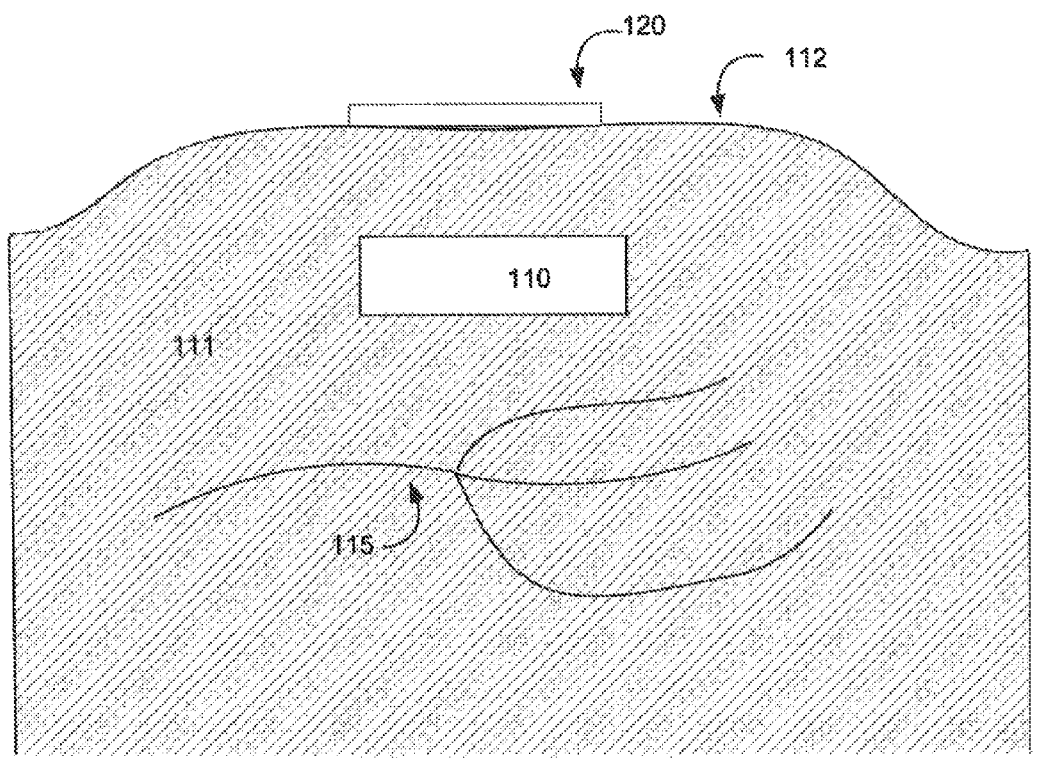
FIG. 1 diagrammatically illustrates an implant unit and external unit, according to an exemplary embodiment of the present disclosure.

FIG. 1 illustrates an implant unit and external unit, according to an exemplary embodiment of the present disclosure. An implant unit 110, may be configured for implantation in a subject, in a location that permits it to modulate a nerve 115. The implant unit 110 may be located in a subject such that intervening tissue 111 exists between the implant unit 110 and the nerve 115. Intervening tissue may include muscle tissue, connective tissue, organ tissue, or any other type of biological tissue. Thus, location of implant unit 110 does not require contact with nerve 115 for effective neuromodulation. The implant unit 110 may also be located directly adjacent to nerve 115, such that no intervening tissue 111 exists.

In treating OSA, implant unit 110 may be located on a genioglossus muscle of a patient. Such a location is suitable for modulation of the hypoglossal nerve, branches of which run inside the genioglossus muscle. Implant unit 110 may also be configured for placement in other locations. For example, migraine treatment may require subcutaneous implantation in the back of the neck, near the hairline of a subject, or behind the ear of a subject, to modulate the greater occipital nerve and/or the trigeminal nerve. Treating hypertension may require the implantation of a neuromodulation implant intravascularly inside the renal artery or renal vein (to modulate the parasympathetic renal nerves), either unilaterally or bilaterally, inside the carotid artery or jugular vein (to modulate the glossopharyngeal nerve through the carotid baroreceptors). Alternatively or additionally, treating hypertension may require the implantation of a neuromodulation implant subcutaneously, behind the ear or in the neck, for example, to directly modulate the glossopharyngeal nerve.

External unit 120 may be configured for location external to a patient, either directly contacting, or close to the skin 112 of the patient. External unit 120 may be configured to be affixed to the patient, for example, by adhering to the skin 112 of the patient, or through a band or other device configured to hold external unit 120 in place. Adherence to the skin of external unit 120 may occur such that it is in the vicinity of the location of implant unit 110.

Figure 2:
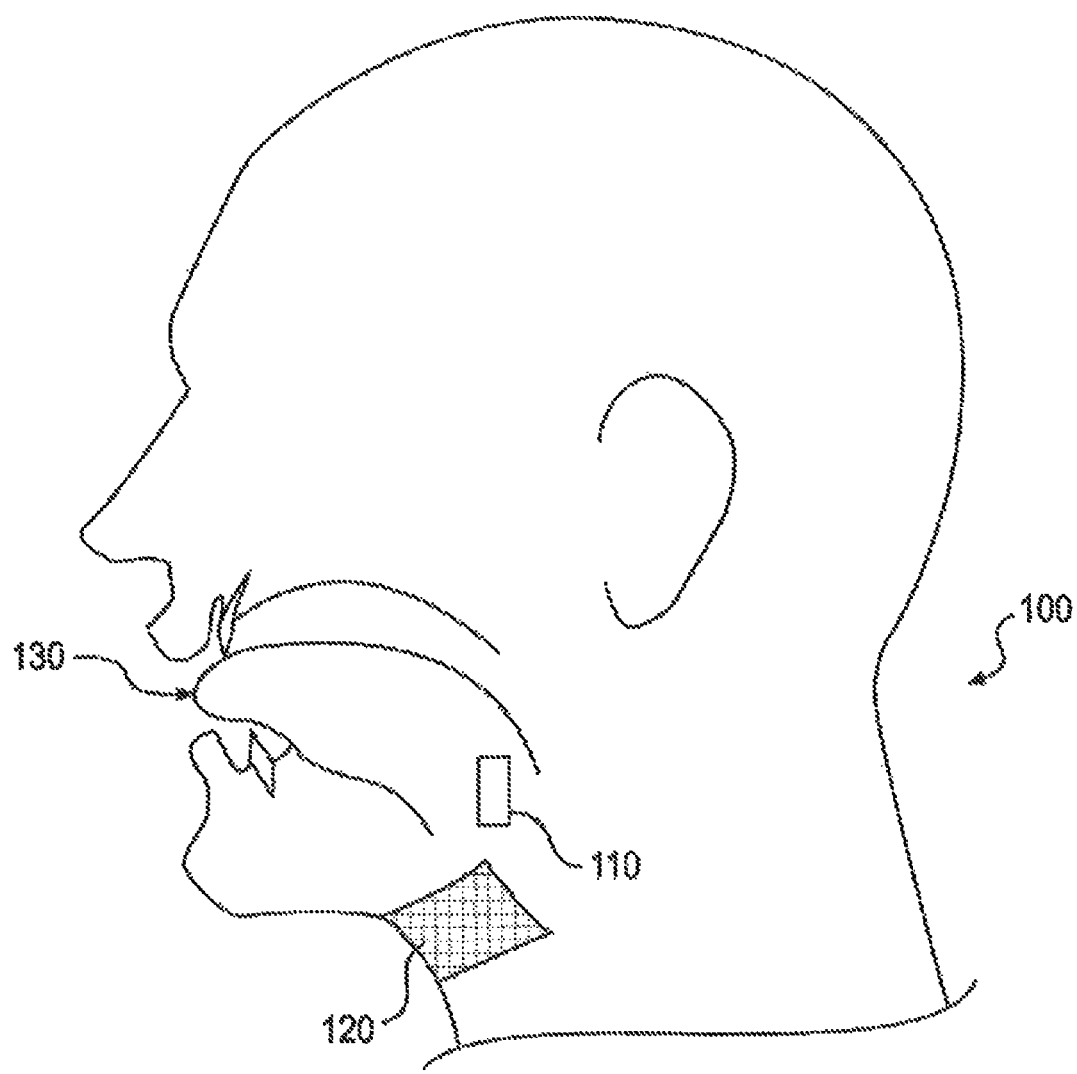
FIG. 2 is a partially cross-sectioned side view of a subject with an implant unit and external unit, according to an exemplary embodiment of the present disclosure.

FIG. 2 illustrates an exemplary embodiment of a neuromodulation system for delivering energy in a patient 100 with OSA. The system may include an external unit 120 that may be configured for location external to the patient. As illustrated in FIG. 2, external unit 120 may be configured to be affixed to the patient 100. FIG. 2 illustrates that in a patient 100 with OSA, the external unit 120 may be configured for placement underneath the patient's chin (e.g., in a location where the external unit in on a side of the patient's skin opposite to a location of terminal fibers of the hypoglossal nerve) and/or on the front of patient's neck. The suitability of placement locations may be determined by communication between external unit 120 and implant unit 110, discussed in greater detail below. In alternate embodiments, for the treatment of conditions other than OSA, the external unit may be configured to be affixed anywhere suitable on a patient, such as the back of a patient's neck, i.e. for communication with a migraine treatment implant unit, on the outer portion of a patient's abdomen, i.e. for communication with a stomach modulating implant unit, on a patient's back, i.e. for communication with a renal artery modulating implant unit, and/or on any other suitable external location on a patient's skin, depending on the requirements of a particular application.

External unit 120 may further be configured to be affixed to an alternative location proximate to the patient. For example, in one embodiment, the external unit may be configured to fixedly or removably adhere to a strap or a band that may be configured to wrap around a part of a patient's body. Alternatively, or in addition, the external unit may be configured to remain in a desired location external to the patient's body without adhering to that location.

The external unit 120 may include a housing. The housing may include any suitable container configured for retaining components. In addition, while the external unit is illustrated schematically in FIG. 2, the housing may be any suitable size and/or shape and may be rigid or flexible. Non-limiting examples of housings for the external unit 100 include one or more of patches, buttons, or other receptacles having varying shapes and dimensions and constructed of any suitable material. In one embodiment, for example, the housing may include a flexible material such that the external unit may be configured to conform to a desired location. For example, as illustrated in FIG. 2, the external unit may include a skin patch, which, in turn, may include a flexible substrate. The material of the flexible substrate may include, but is not limited to, plastic, silicone, woven natural fibers, and other suitable polymers, copolymers, and combinations thereof. Any portion of external unit 120 may be flexible or rigid, depending on the requirements of a particular application.

As previously discussed, in some embodiments external unit 120 may be configured to adhere to a desired location. Accordingly, in some embodiments, at least one side of the housing may include an adhesive material. The adhesive material may include a biocompatible material and may allow for a patient to adhere the external unit to the desired location and remove the external unit upon completion of use. The adhesive may be configured for single or multiple uses of the external unit. Suitable adhesive materials may include, but are not limited to biocompatible glues, starches, elastomers, thermoplastics, and emulsions.

Figure 3:
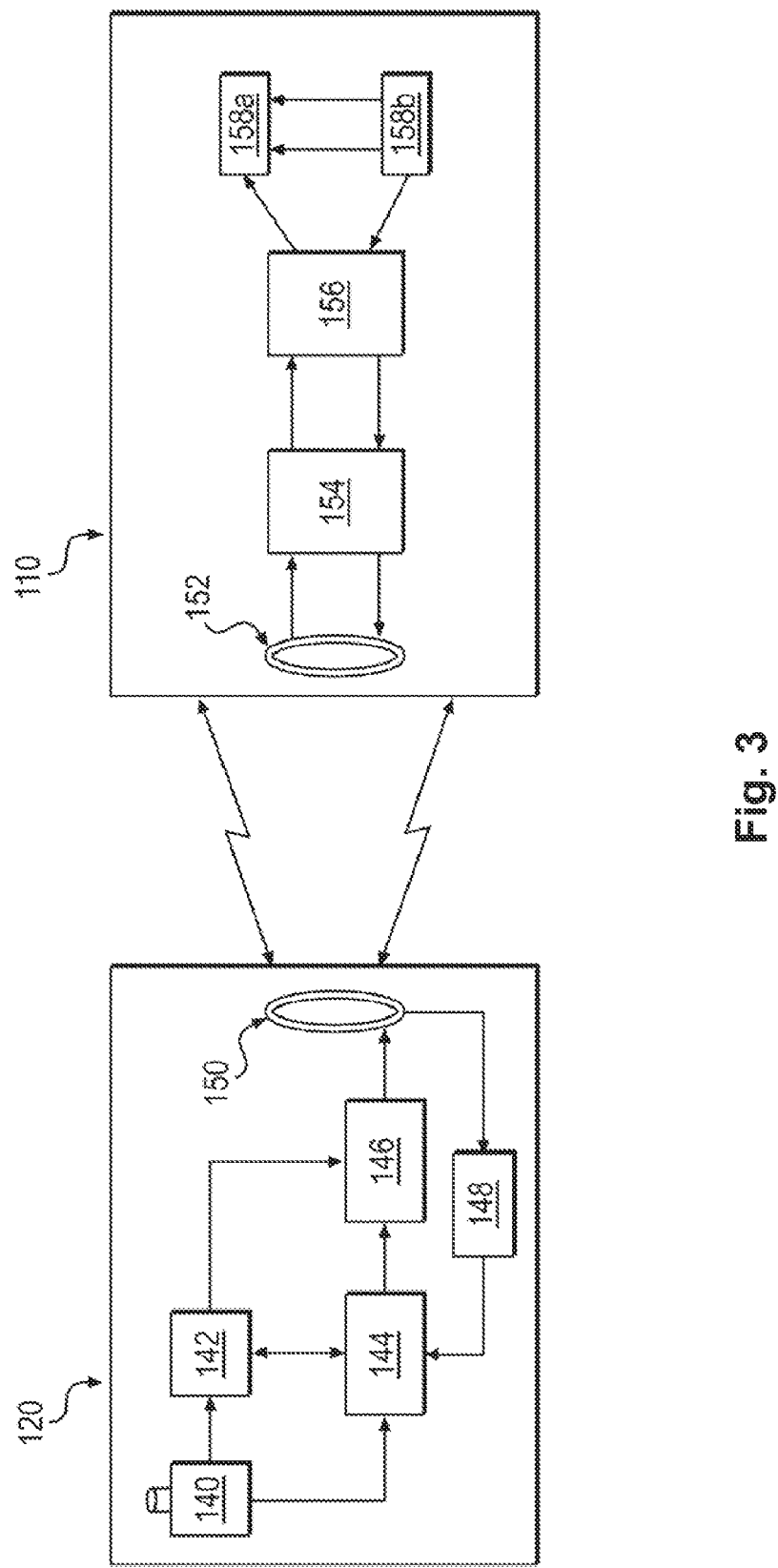
FIG. 3 diagrammatically illustrates a system including an implant unit and an external unit, according to an exemplary embodiment of the present disclosure.

FIG. 3 schematically illustrates a system including external unit 120 and an implant unit 110. In some embodiments, internal unit 110 may be configured as a unit to be implanted into the body of a patient, and external unit 120 may be configured to send signals to and/or receive signals from implant unit 110.

As shown in FIG. 3, various components may be included within a housing of external unit 120 or otherwise associated with external unit 120. As illustrated in FIG. 3, at least one processor 144 may be associated with external unit 120. For example, the at least one processor 144 may be located within the housing of external unit 120. In alternative embodiments, the at least one processor may be configured for wired or wireless communication with the external unit from a location external to the housing.

The at least one processor may include any electric circuit that may be configured to perform a logic operation on at least one input variable. The at least one processor may therefore include one or more integrated circuits, microchips, microcontrollers, and microprocessors, which may be all or part of a central processing unit (CPU), a digital signal processor (DSP), a field programmable gate array (FPGA), or any other circuit known to those skilled in the art that may be suitable for executing instructions or performing logic operations.

FIG. 3 illustrates that the external unit 120 may further be associated with a power source 140. The power source may be removably coupled to the external unit at an exterior location relative to external unit. Alternatively, as shown in FIG. 3, power source 140 may be permanently or removably coupled to a location within external unit 120. The power source may further include any suitable source of power configured to be in electrical communication with the processor. In one embodiment, for example the power source 140 may include a battery.

The power source may be configured to power various components within the external unit. As illustrated in FIG. 3, power source 140 may be configured to provide power to the processor 144. In addition, the power source 140 may be configured to provide power to a signal source 142. The signal source 142 may be in communication with the processor 144 and may include any device configured to generate a signal (e.g., a sinusoidal signal, square wave, triangle wave, microwave, radio-frequency (RF) signal, or any other type of electromagnetic signal). Signal source 142 may include, but is not limited to, a waveform generator that may be configured to generate alternating current (AC) signals and/or direct current (DC) signals. In one embodiment, for example, signal source 142 may be configured to generate an AC signal for transmission to one or more other components. Signal source 142 may be configured to generate a signal of any suitable frequency. In some embodiments, signal source 142 may be configured to generate a signal having a frequency of from about 6.5 MHz to about 13.6 MHz. In additional embodiments, signal source 142 may be configured to generate a signal having a frequency of from about 7.4 to about 8.8 MHz. In further embodiments, signal source 142 may generate a signal having a frequency as low as 90 kHz or as high as 28 MHz.

Signal source 142 may be configured for direct or indirect electrical communication with an amplifier 146. The amplifier may include any suitable device configured to amplify one or more signals generated from signal source 142. Amplifier 146 may include one or more of various types of amplification devices, including, for example, transistor based devices, operational amplifiers, RF amplifiers, power amplifiers, or any other type of device that can increase the gain associated one or more aspects of a signal. The amplifier may further be configured to output the amplified signals to one or more components within external unit 120.

The external unit may additionally include a primary antenna 150. The primary antenna may be configured as part of a circuit within external unit 120 and may be coupled either directly or indirectly to various components in external unit 120. For example, as shown in FIG. 3, primary antenna 150 may be configured for communication with the amplifier 146.

The primary antenna may include any conductive structure that may be configured to create an electromagnetic field. The primary antenna may further be of any suitable size, shape, and/or configuration. The size, shape, and/or configuration may be determined by the size of the patient, the placement location of the implant unit, the size and/or shape of the implant unit, the amount of energy required to modulate a nerve, a location of a nerve to be modulated, the type of receiving electronics present on the implant unit, etc. The primary antenna may include any suitable antenna known to those skilled in the art that may be configured to send and/or receive signals. Suitable antennas may include, but are not limited to, a long-wire antenna, a patch antenna, a helical antenna, etc. In one embodiment, for example, as illustrated in FIG. 3, primary antenna 150 may include a coil antenna. Such a coil antenna may be made from any suitable conductive material and may be configured to include any suitable arrangement of conductive coils (e.g., diameter, number of coils, layout of coils, etc.). A coil antenna suitable for use as primary antenna 150 may have a diameter of between about 1 cm and 10 cm, and may be circular or oval shaped. In some embodiments, a coil antenna may have a diameter between 5 cm and 7 cm, and may be oval shaped. A coil antenna suitable for use as primary antenna 150 may have any number of windings, e.g. 4, 8, 12, or more. A coil antenna suitable for use as primary antenna 150 may have a wire diameter between about 0.1 mm and 2 mm. These antenna parameters are exemplary only, and may be adjusted above or below the ranges given to achieve suitable results.

As noted, implant unit 110 may be configured to be implanted in a patient's body (e.g., beneath the patient's skin). FIG. 2 illustrates that the implant unit 110 may be configured to be implanted for modulation of a nerve associated with a muscle of the subject's tongue 130. For example, implant unit 110 may be configured to modulate a hypoglossal nerve of a subject, e.g., through interaction with terminal fibers of the hypoglossal nerve. Modulating a nerve associated with a muscle of the subject's tongue 130 may include stimulation to cause a muscle contraction. In further embodiments, the implant unit may be configured to be placed in conjunction with any nerve that one may desire to modulate. For example, modulation of the occipital nerve, the greater occipital nerve, and/or the trigeminal nerve may be useful for treating pain sensation in the head, such as that from migraines. Modulation of parasympathetic nerve fibers on and around the renal arteries (i.e. the renal nerves), the vagus nerve, and/or the glossopharyngeal nerve may be useful for treating hypertension. Additionally, any nerve of the peripheral nervous system (both spinal and cranial), including motor neurons, sensory neurons, sympathetic neurons and parasympathetic neurons, may be modulated to achieve a desired effect.

Implant unit 110 may be formed of any materials suitable for implantation into the body of a patient. In some embodiments, implant unit 110 may include a flexible carrier 161 (FIG. 4) including a flexible, biocompatible material. Such materials may include, for example, silicone, polyimides, phenyltrimethoxysilane (PTMS), polymethyl methacrylate (PMMA), Parylene C, polyimide, liquid polyimide, laminated polyimide, black epoxy, polyether ether ketone (PEEK), Liquid Crystal Polymer (LCP), Kapton, etc. Implant unit 110 may further include circuitry including conductive materials, such as gold, platinum, titanium, or any other biocompatible conductive material or combination of materials. Implant unit 110 and flexible carrier 161 may also be fabricated with a thickness suitable for implantation under a patient's skin. Implant 110 may have thickness of less than about 4 mm or less than about 2 mm.

Other components that may be included in or otherwise associated with the implant unit are illustrated in FIG. 3. For example, implant unit 110 may include a secondary antenna 152 mounted onto or integrated with flexible carrier 161. Similar to the primary antenna, the secondary antenna may include any suitable antenna known to those skilled in the art that may be configured to send and/or receive signals. The secondary antenna may include any suitable size, shape, and/or configuration. The size, shape and/or configuration may be determined by the size of the patient, the placement location of the implant unit, the amount of energy required to modulate the nerve, etc. Suitable antennas may include, but are not limited to, a long-wire antenna, a patch antenna, a helical antenna, etc. In some embodiments, for example, secondary antenna 152 may include a coil antenna having a circular shape (see also FIG. 4) or oval shape. Such a coil antenna may be made from any suitable conductive material and may be configured to include any suitable arrangement of conductive coils (e.g., diameter, number of coils, layout of coils, etc.). A coil antenna suitable for use as secondary antenna 152 may have a diameter of between about 5 mm and 30 mm, and may be circular or oval shaped. A coil antenna suitable for use as secondary antenna 152 may have any number of windings, e.g. 4, 15, 20, 30, or 50. A coil antenna suitable for use as secondary antenna 152 may have a wire diameter between about 0.01 mm and 1 mm. These antenna parameters are exemplary only, and may be adjusted above or below the ranges given to achieve suitable results.

Figures 10A, 10B:
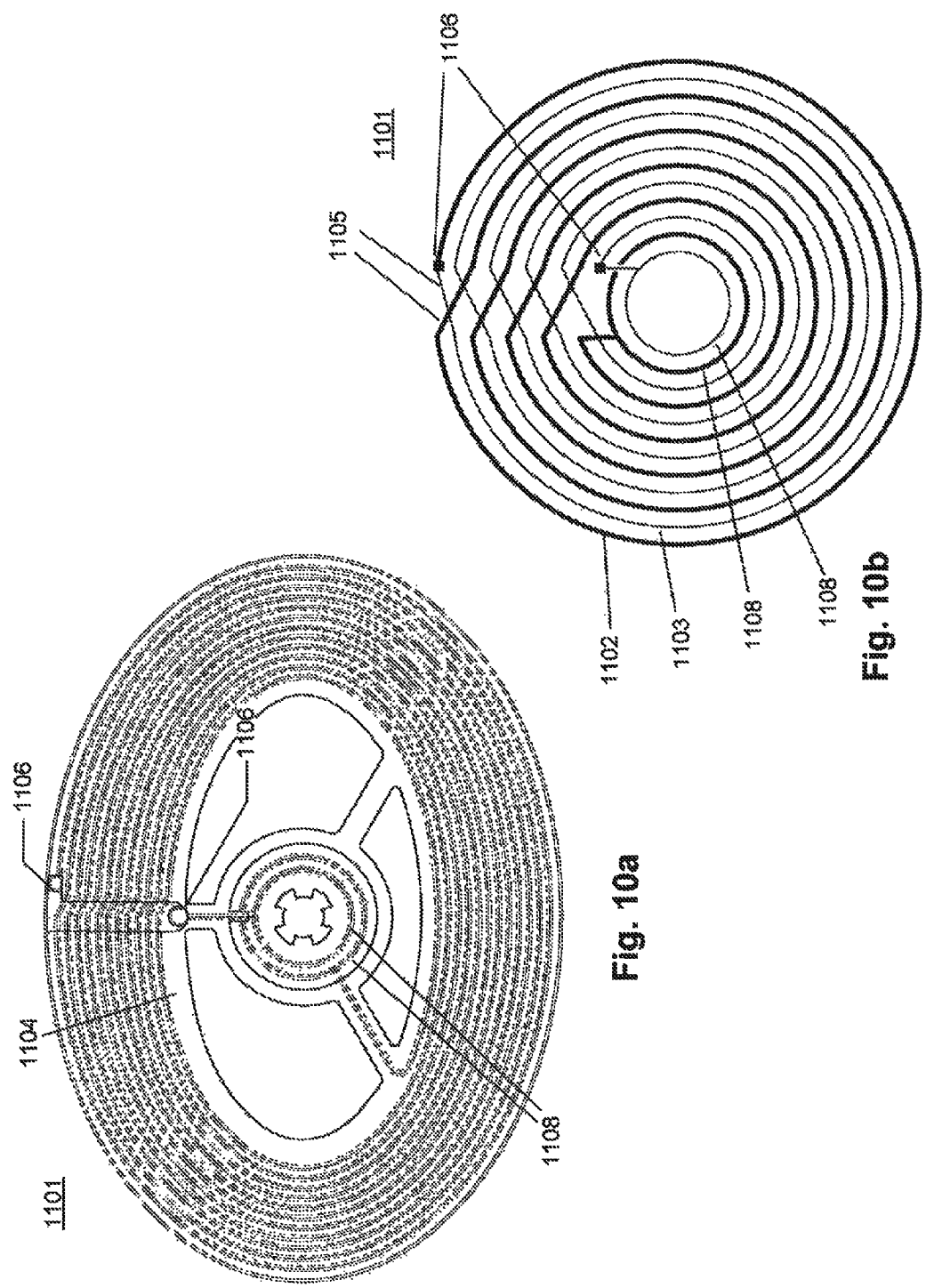
FIGS. 10a and 10b illustrate a double-layer crossover antenna according to exemplary embodiments of the present disclosure.

FIGS. 10*a* and 10*b* illustrate an exemplary double-layer crossover antenna 1101 suitable for use as either primary antenna 150 or secondary antenna 152. While a double-layer crossover antenna is shown and described, other antenna configurations may be suitable for primary antenna 150 and/or secondary antenna 152. For example, single layer antennas may be used where antenna components (e.g., coils) are arranged in a single layer, e.g., either on or within a dielectric or insulating material. Also, while a crossover pattern is shown, other patterns may also be suitable. For example, in some embodiments, a wire associated with primary antenna 150 and/or secondary antenna 152 may include a pattern of traces of progressively decreasing dimension. In the case of traces arranged in coils, for example, each loop could include rings of progressively decreasing diameter to create a pattern that spirals inwardly. A similar approach may be viable using traces of other shapes as well.

Returning to FIG. 10*a*, this figure illustrates a single coil of double-layer crossover antenna 1101, while FIG. 10*b* illustrates two layers of double layer crossover antenna 1101. Antenna 1101 may include a first coil of wire 1102 arranged on a first side of a dielectric carrier 1104 and a second coil of wire 1103 on a second side of a dielectric carrier 1104.

Arranging the antenna coils in a double layer may serve to increase the transmission range of the antenna without increasing the size of the antenna. Such an arrangement, however, may also serve to increase capacitance between the wires of each coil. In each wire coil, an amount of parasitic capacitance between wires may partially depend on the distance each wire is from its neighbor. In a single layer coil, capacitance may be generated between each loop of the coil and its neighbors to either side. Thus, more compact coils may generate more parasitic capacitance. When a second layer coil is added, additional capacitance may then be generated between the wires of the first coil and the wires of the second coil. This additional capacitance may be further increased if corresponding loops of the first and second coils have the same or similar diameters, and/or if a dielectric carrier separating the loops is made very thin. Increased parasitic capacitance in an antenna may serve to alter characteristics, such as resonant frequency, of the antenna in unpredictable amounts based on manufacturing specifications. Additionally, resonant frequency drift, caused, for example by moisture incursion or antenna flexing, may be increased by the presence of increased parasitic capacitance. Thus, in order to decrease variability in the manufactured product, it may be advantageous to reduce the levels of parasitic capacitance in a dual layer antenna.

FIG. 10*b* illustrates a double layer crossover antenna 1101 which may serve to reduce the parasitic capacitance in a manufactured antenna. As illustrated in FIG. 10*b*, a first coil of wire 1102 is concentrically offset from a second coil of wire 1103. In contrast to a configuration where each loop of a first coil 1102 has the same diameter as corresponding loop of the second coil 1103, concentrically offsetting corresponding loops of each wire coil serves to increase the distance between a single loop of the first coil 1102 with a corresponding loop of the second coil 1103. This increased distance, in turn, may decrease the parasitic wire-to-wire capacitance between loops of first coil 1102 and corresponding loops of second coil 1103. This configuration may be particularly advantageous in reducing parasitic capacitance in a situation where a dielectric carrier 1104 is thin enough such that the concentric distance by which each coil is offset is relatively large compared to the thickness of the dielectric carrier 1104. For example, in a situation where a dielectric carrier is 0.5 mm thick, a concentric offset of 0.5 mm or more may produce a large change in parasitic capacitance. In contrast, in a situation where a dielectric carrier is 5 mm thick, a concentric offset of 0.5 mm may produce a smaller change in parasitic capacitance. The concentric offset between a first coil 1102 and a second coil 1103 may be achieved, for example, by a plurality of electrical trace steps 1105 that offset each loop of the coils from each preceding loop. Electrical trace steps 1105 on a first side of dielectric carrier 1104 cross over electrical trace steps 1105 on a second side of dielectric carrier 1104, thus providing the crossover feature of double-layer crossover antenna 1101.

In additional embodiments, double layer crossover antenna 1101 may include openings 1106 in dielectric carrier 1104 to facilitate the electrical connection of first and second coils 1102, 1103. First and second coils 1102, 1103 of double layer crossover antenna 1101 may also include exposed electrical portions 1108 configured to electrically connect with a connector of a device housing that may be coupled to antenna 1101. Exposed electrical portions 1108 may be configured so as to maintain electrical contact with the connector of a device housing independent of the axial orientation of the connection. As shown in FIG. 10*a*, for example, exposed electrical portions 1108 may be configured as continuous or discontinuous circles in order to achieve this. A first exposed electrical portion 1108 configured as a discontinuous circle may provide a space through which an electrical trace may pass without contacting the first exposed electrical portion, for example to connect with a second exposed electrical portion located inside the first, or to other components located within the circle of the first exposed electrical portion 1108. FIG. 10*a* illustrates an antenna having substantially elliptical coils; other shapes, such as circular, triangular, square, etc., may be also be used in different embodiments. Elliptical coils may facilitate placement of external unit 120 in certain areas (e.g., under the chin of a subject) while maintaining desirable electrical performance characteristics.

FIGS. 11*a* and 11*b* illustrate an exemplary embodiment of external unit 120, including features that may be found in any combination in other embodiments. FIG. 11*a* illustrates a side view of external unit 120, depicting carrier 1201 and electronics housing 1202.

Carrier 1201 may include a skin patch configured for adherence to the skin of a subject, for example through adhesives of mechanical means. Carrier 1201 may be flexible or rigid, or may have flexible portions and rigid portions. Carrier 1201 and may include a primary antenna 150, for example, a double-layer crossover antenna 1101 such as that illustrated in FIGS. 10*a* and 10*b*. Carrier 1201 may also include power source 140, such as a paper battery, thin film battery, or other type of substantially flat and/or flexible battery. Carrier 1201 may also include any other type of battery or power source. Carrier 1201 may also include a connector 1203 configured for selectively or removably connecting carrier 1201 to electronics housing 1202. Connector 1203 may extend or protrude from carrier 1201. Connector 1203 may be configured to be received by a recess 1204 of electronics housing 1202 Connector 1203 may be configured as a non-pouch connector, configured to provide a selective connection to electronics housing 1204 without the substantial use of concave feature. Connector 1203 may include, for example a peg, and may have flexible arms. Connector 1203 may further include a magnetic connection, a velcro connection, and/or a snap dome connection. Connector 1203 may also include a locating feature, configured to locate electronics housing 1202 at a specific height, axial location, and/or axial orientation with respect to carrier 1201. A locating feature of connector 1203 may further include pegs, rings, boxes, ellipses, bumps, etc. Connector 1203 may be centered on carrier 1201, may be offset from the center by a predetermined amount, or may be provided at any other suitable location of carrier 1201. Multiple connectors 1203 may be provided on carrier 1201. Connector 1203 may be configured such that removal from electronics housing 1202 causes breakage of connector 1203. Such a feature may be desirable to prevent re-use of carrier 1201, which may lose some efficacy through continued use.

Electronics housing 1202 is illustrated in side view in FIG. 11*a* and in a bottom view in FIG. 11*b*. Electronics housing 1202 may include electronics portion 1205, which may be arranged inside electronics housing 1202 in any manner that is suitable. Electronics portion 1205 may include various components, further discussed below, of external unit 120. For example, electronics portion 1205 may include any combination of at least one processor 144 associated with external unit 120, a power source 140, such as a battery, a primary antenna 152, and an electrical circuit 170. Electronics portion 1205 may also include any other component described herein as associated with external unit 120. Additional components may also be recognized by those of skill in the art.

Electronics housing 1202 may include a recess 1204 configured to receive connector 1203. Electronics housing 1202 may include at least one electrical connector 1210, 1211, 1212. Electrical connectors 1210, 1211, 1212 may be arranged with pairs of electrical contacts, as shown in FIG. 11*b*, or with any other number of electrical contacts. The pair of electrical contacts of each electrical connector 1210, 1211, 1212 may be continuously electrically connected with each other inside of housing 1202, such that the pair of electrical contacts represents a single connection point to a circuit. In such a configuration, it is only necessary that one of the electrical contacts within a pair be connected. Electrical connectors 1210, 1211, and 1212 may thus include redundant electrical contacts. The electrical contacts of each electrical connector 1210, 1211, 1212 may also represent opposite ends of a circuit, for example, the positive and negative ends of a battery charging circuit. In an exemplary embodiment, as shown in FIG. 11*b*, electrical connectors 1210, 1211, and 1212 are configured so as to maintain electrical contact with an exposed electrical portion 1108 independent of an axial orientation of electronics housing 1202. Connection between any or all of electrical connectors 1210, 1211, 1212 and exposed electrical portions 1108 may thus be established and maintained irrespective of relative axial positions of carrier 1201 and housing 1202. Thus, when connector 1203 is received by recess 1204, housing 1202 may rotate with respect to carrier 1201 without interrupting electrical contact between at least one of electrical connectors 1210, 1211, 1212 and exposed electrical portions 1108. Axial orientation independence may be achieved, for example, through the use of circular exposed electrical portions 1108 and each of a pair of contacts of electrical connectors 1210, 1211, 1212 disposed equidistant from a center of recess 1204 at a radius approximately equal to that of a corresponding exposed electrical portion 1108. In this fashion, even if exposed electrical portion 1108 includes a discontinuous circle, at least one electrical contact of electrical connectors 1210, 1211, and 1212 may make contact. In FIG. 11*b*, electrical connectors 1210, 1211, 1212 are illustrated as pairs of rectangular electrical contacts. Electrical connectors 1210, 1211, 1212, however, may include any number of contacts, be configured as continuous or discontinuous circles, or have any other suitable shape or configuration.

One exemplary embodiment may operate as follows. As shown in FIG. 11*b*, electronics housing 1202 may include more electrical connectors 1210, 1211, 1212, than a carrier 1201 includes exposed electrical portions 1108. In the illustrated embodiments, electronics housing 1202 includes three electrical connectors 1210, 1211, and 1212, while a double-layer crossover antenna 1101 includes two exposed electrical portions 1108. In such an embodiment, two electrical connectors 1211 and 1212 may be configured with continuously electrically connected electrical contacts, such that each connector makes contact with a different exposed electrical portion 1108, where the exposed electrical portions 1108 represent opposite ends of double layer crossover antenna 1101. Thus, antenna 1101 may be electrically connected to the electrical components contained in electronics portion 1205. When connected to carrier 1201 in this configuration, electrical connectors 1210 may not make contact with any electrodes. In this embodiment, electrical connectors 1210 may be reserved to function as opposite ends of a battery charging circuit, in order to charge a battery contained in electronics portion 1205 when electronics housing 1202 is not being used for therapy. A battery charger unit may be provided with a non-breakable connector similar to that of non-pouch connector 1203, and configured to engage with recess 1204. Upon engaging with recess 1204, electrode contacts of the battery charger unit may contact electrical connectors 1210 to charge a battery contained within electronics portion 1205.

In an additional embodiment consistent with the present disclosure, an activator chip may include electronics housing 1202. Processor 144 may be configured to activate when at least one of electrical connectors 1210, 1211, 1212 contact exposed electrical portions 1108 included in carrier 1201. In this manner, an electronics housing 1202 may be charged and left dormant for many days prior to activation. Simply connecting electronics housing 1202 to carrier 1201 (and inducing contact between an electrical connector 1210, 1211, 1212 and an electrode portion 1108) may cause the processor to activate. Upon activation, processor 144 may be configured to enter a specific mode of operation, such as a calibration mode (for calibrating the processor after placement of the carrier on the skin), a placement mode (for assisting a user to properly place the carrier on the skin), and/or a therapy mode (to begin a therapy session). The various modes of processor 144 may include waiting periods at the beginning, end, or at any time during. For example, a placement mode may include a waiting period at the end of the mode to provide a period during which a subject may fall asleep. A therapy mode may include a similar waiting period at the beginning of the mode. Additionally or alternatively, processor 144 may be configured to provide waiting periods separate from the described modes, in order to provide a desired temporal spacing between system activities.

Figure 4:
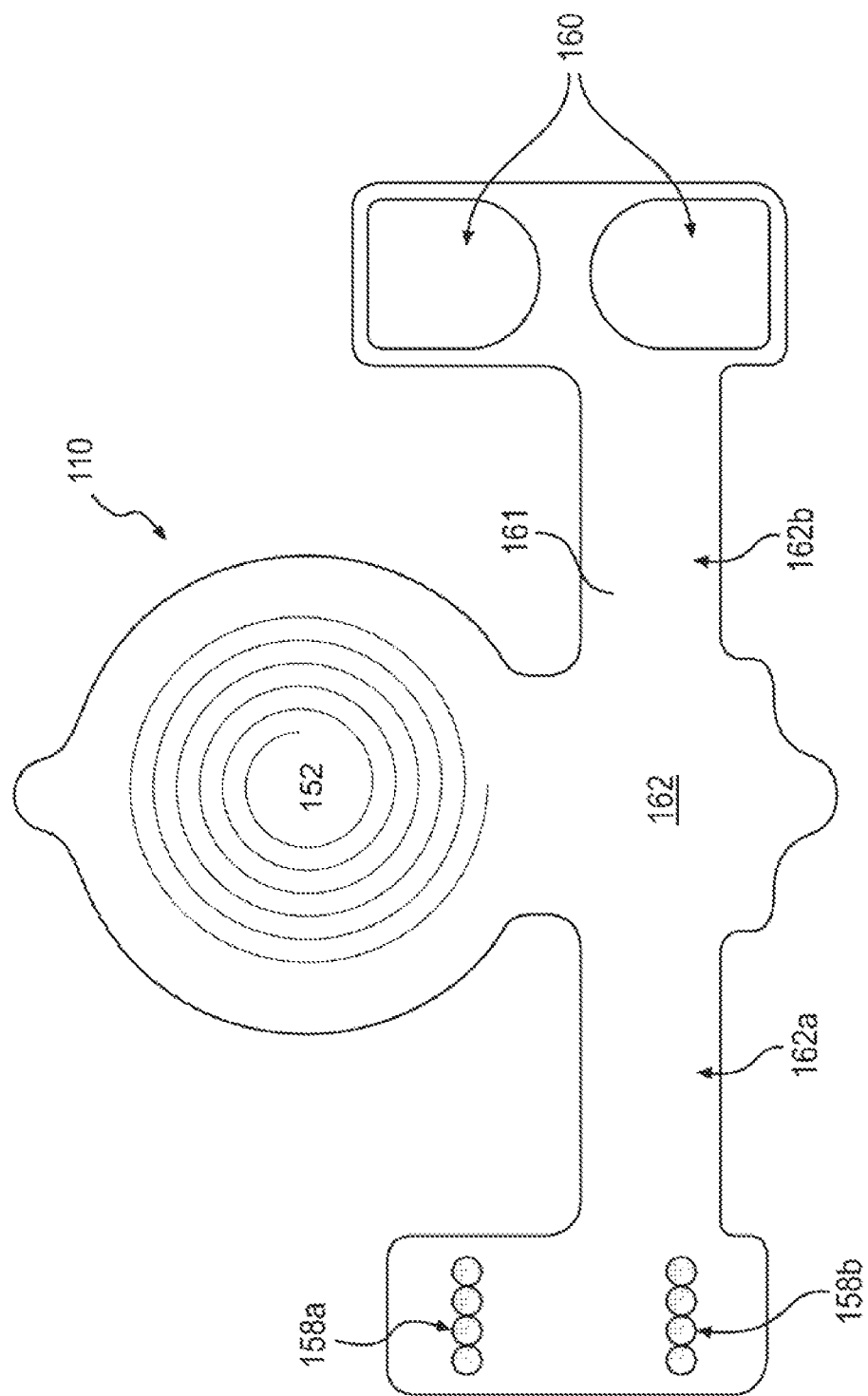
FIG. 4 is a top view of an implant unit, according to an exemplary embodiment of the present disclosure.

Implant unit 110 may additionally include a plurality of field-generating implant electrodes 158*a*, 158*b*. The electrodes may include any suitable shape and/or orientation on the implant unit so long as the electrodes may be configured to generate an electric field in the body of a patient. Implant electrodes 158*a* and 158*b* may also include any suitable conductive material (e.g., copper, silver, gold, platinum, iridium, platinum-iridium, platinum-gold, conductive polymers, etc.) or combinations of conductive (and/or noble metals) materials. In some embodiments, for example, the electrodes may include short line electrodes, circular electrodes, and/or circular pairs of electrodes. As shown in FIG. 4, electrodes 158*a* and 158*b* may be located on an end of a first extension 162*a* of an elongate arm 162. The electrodes, however, may be located on any portion of implant unit 110. Additionally, implant unit 110 may include electrodes located at a plurality of locations, for example on an end of both a first extension 162*a* and a second extension 162*b* of elongate arm 162, as illustrated, for example, in FIG. 5. Implant electrodes may have a thickness between about 200 nanometers and 1 millimeter. Anode and cathode electrode pairs may be spaced apart by about a distance of about 0.2 mm to 25 mm. In additional embodiments, anode and cathode electrode pairs may be spaced apart by a distance of about 1 mm to 10 mm, or between 4 mm and 7 mm. Adjacent anodes or adjacent cathodes may be spaced apart by distances as small as 0.001 mm or less, or as great as 25 mm or more. In some embodiments, adjacent anodes or adjacent cathodes may be spaced apart by a distance between about 0.2 mm and 1 mm.

FIG. 4 provides a schematic representation of an exemplary configuration of implant unit 110. As illustrated in FIG. 4, in one embodiment, the field-generating electrodes 158a and 158b may include two sets of four circular electrodes, provided on flexible carrier 161, with one set of electrodes providing an anode and the other set of electrodes providing a cathode. Implant unit 110 may include one or more structural elements to facilitate implantation of implant unit 110 into the body of a patient. Such elements may include, for example, elongated arms, suture holes, polymeric surgical mesh, biological glue, spikes of flexible carrier protruding to anchor to the tissue, spikes of additional biocompatible material for the same purpose, etc. that facilitate alignment of implant unit 110 in a desired orientation within a patient's body and provide attachment points for securing implant unit 110 within a body. For example, in some embodiments, implant unit 110 may include an elongate arm 162 having a first extension 162a and, optionally, a second extension 162b. Extensions 162a and 162b may aid in orienting implant unit 110 with respect to a particular muscle (e.g., the genioglossus muscle), a nerve within a patient's body, or a surface within a body above a nerve. For example, first and second extensions 162a, 162b may be configured to enable the implant unit to conform at least partially around soft or hard tissue (e.g., nerve, bone, or muscle, etc.) beneath a patient's skin. Further, implant unit 110 may also include one or more suture holes 160 located anywhere on flexible carrier 161. For example, in some embodiments, suture holes 160 may be placed on second extension 162b of elongate arm 162 and/or on first extension 162a of elongate arm 162. Implant unit 110 may be constructed in various shapes. Additionally, or alternatively, implant unit 110 may include surgical mesh 1050 or other perforatable material. In some embodiments, implant unit may appear substantially as illustrated in FIG. 4. In other embodiments, implant unit 110 may lack illustrated structures such as second extension 162b, or may have additional or different structures in different orientations. Additionally, implant unit 110 may be formed with a generally triangular, circular, or rectangular shape, as an alternative to the winged shape shown in FIG. 4. In some embodiments, the shape of implant unit 110 (e.g., as shown in FIG. 4) may facilitate orientation of implant unit 110 with respect to a particular nerve to be modulated. Thus, other regular or irregular shapes may be adopted in order to facilitate implantation in differing parts of the body.

Figure 5:
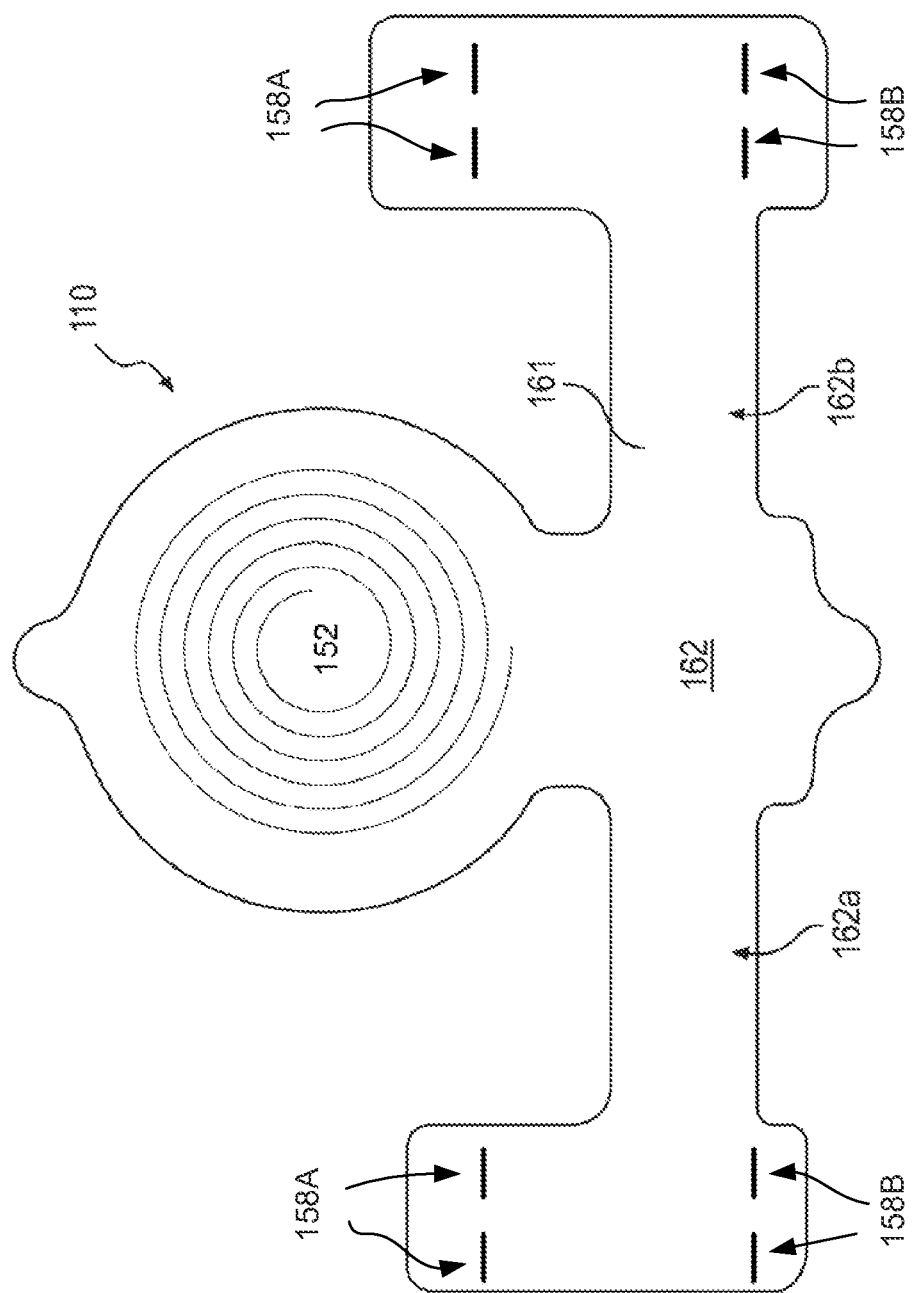
FIG. 5 is a top view of an another embodiment of an implant unit, according to an exemplary embodiment of the present disclosure.

As illustrated in FIG. 4, secondary antenna 152 and electrodes 158a, 158b may be mounted on or integrated with flexible carrier 161. Various circuit components and connecting wires (discussed further below) may be used to connect secondary antenna with implant electrodes 158a and 158b. To protect the antenna, electrodes, circuit components, and connecting wires from the environment within a patient's body, implant unit 110 may include a protective coating that encapsulates implant unit 110. In some embodiments, the protective coating may be made from a flexible material to enable bending along with flexible carrier 161. The encapsulation material of the protective coating may also resist humidity penetration and protect against corrosion. In some embodiments, the protective coating may include a plurality of layers, including different materials or combinations of materials in different layers FIG. 5 is a perspective view of an alternate embodiment of an implant unit 110, according to an exemplary embodiment of the present disclosure. As illustrated in FIG. 5, implant unit 110 may include a plurality of electrodes, located, for example, at the ends of first extension 162a and second extension 162b. FIG. 5 illustrates an embodiment wherein implant electrodes 158a and 158b include short line electrodes.

Returning to FIGS. 2 and 3, external unit 120 may be configured to communicate with implant unit 110. For example, in some embodiments, a primary signal may be generated on primary antenna 150, using, e.g., processor 144, signal source 142, and amplifier 146. More specifically, in one embodiment, power source 140 may be configured to provide power to one or both of the processor 144 and the signal source 142. The processor 144 may be configured to cause signal source 142 to generate a signal (e.g., an RF energy signal). Signal source 142 may be configured to output the generated signal to amplifier 146, which may amplify the signal generated by signal source 142. The amount of amplification and, therefore, the amplitude of the signal may be controlled, for example, by processor 144. The amount of gain or amplification that processor 144 causes amplifier 146 to apply to the signal may depend on a variety of factors, including, but not limited to, the shape, size, and/or configuration of primary antenna 150, the size of the patient, the location of implant unit 110 in the patient, the shape, size, and/or configuration of secondary antenna 152, a degree of coupling between primary antenna 150 and secondary antenna 152 (discussed further below), a desired magnitude of electric field to be generated by implant electrodes 158a, 158b, etc. Amplifier 146 may output the amplified signal to primary antenna 150.

External unit 120 may communicate a primary signal on primary antenna to the secondary antenna 152 of implant unit 110. This communication may result from coupling between primary antenna 150 and secondary antenna 152. Such coupling of the primary antenna and the secondary antenna may include any interaction between the primary antenna and the secondary antenna that causes a signal on the secondary antenna in response to a signal applied to the primary antenna. In some embodiments, coupling between the primary and secondary antennas may include capacitive coupling, inductive coupling, radiofrequency coupling, etc. and any combinations thereof.

Coupling between primary antenna 150 and secondary antenna 152 may depend on the proximity of the primary antenna relative to the secondary antenna. That is, in some embodiments, an efficiency or degree of coupling between primary antenna 150 and secondary antenna 152 may depend on the proximity of the primary antenna to the secondary antenna. The proximity of the primary and secondary antennas may be expressed in terms of a coaxial offset (e.g., a distance between the primary and secondary antennas when central axes of the primary and secondary antennas are co-aligned), a lateral offset (e.g., a distance between a central axis of the primary antenna and a central axis of the secondary antenna), and/or an angular offset (e.g., an angular difference between the central axes of the primary and secondary antennas). In some embodiments, a theoretical maximum efficiency of coupling may exist between primary antenna 150 and secondary antenna 152 when both the coaxial offset, the lateral offset, and the angular offset are zero. Increasing any of the coaxial offset, the lateral offset, and the angular offset may have the effect of reducing the efficiency or degree of coupling between primary antenna 150 and secondary antenna 152.

As a result of coupling between primary antenna 150 and secondary antenna 152, a secondary signal may arise on secondary antenna 152 when the primary signal is present on the primary antenna 150. Such coupling may include inductive/magnetic coupling, RF coupling/transmission, capacitive coupling, or any other mechanism where a secondary signal may be generated on secondary antenna 152 in response to a primary signal generated on primary antenna 150. Coupling may refer to any interaction between the primary and secondary antennas. In addition to the coupling between primary antenna 150 and secondary antenna 152, circuit components associated with implant unit 110 may also affect the secondary signal on secondary antenna 152. Thus, the secondary signal on secondary antenna 152 may refer to any and all signals and signal components present on secondary antenna 152 regardless of the source.

While the presence of a primary signal on primary antenna 150 may cause or induce a secondary signal on secondary antenna 152, the coupling between the two antennas may also lead to a coupled signal or signal components on the primary antenna 150 as a result of the secondary signal present on secondary antenna 152. A signal on primary antenna 150 induced by a secondary signal on secondary antenna 152 may be referred to as a primary coupled signal component. The primary signal may refer to any and all signals or signal components present on primary antenna 150, regardless of source, and the primary coupled signal component may refer to any signal or signal component arising on the primary antenna as a result of coupling with signals present on secondary antenna 152. Thus, in some embodiments, the primary coupled signal component may contribute to the primary signal on primary antenna 150.

Implant unit 110 may be configured to respond to external unit 120. For example, in some embodiments, a primary signal generated on primary coil 150 may cause a secondary signal on secondary antenna 152, which in turn, may cause one or more responses by implant unit 110. In some embodiments, the response of implant unit 110 may include the generation of an electric field between implant electrodes 158a and 158b.

Figure 6:
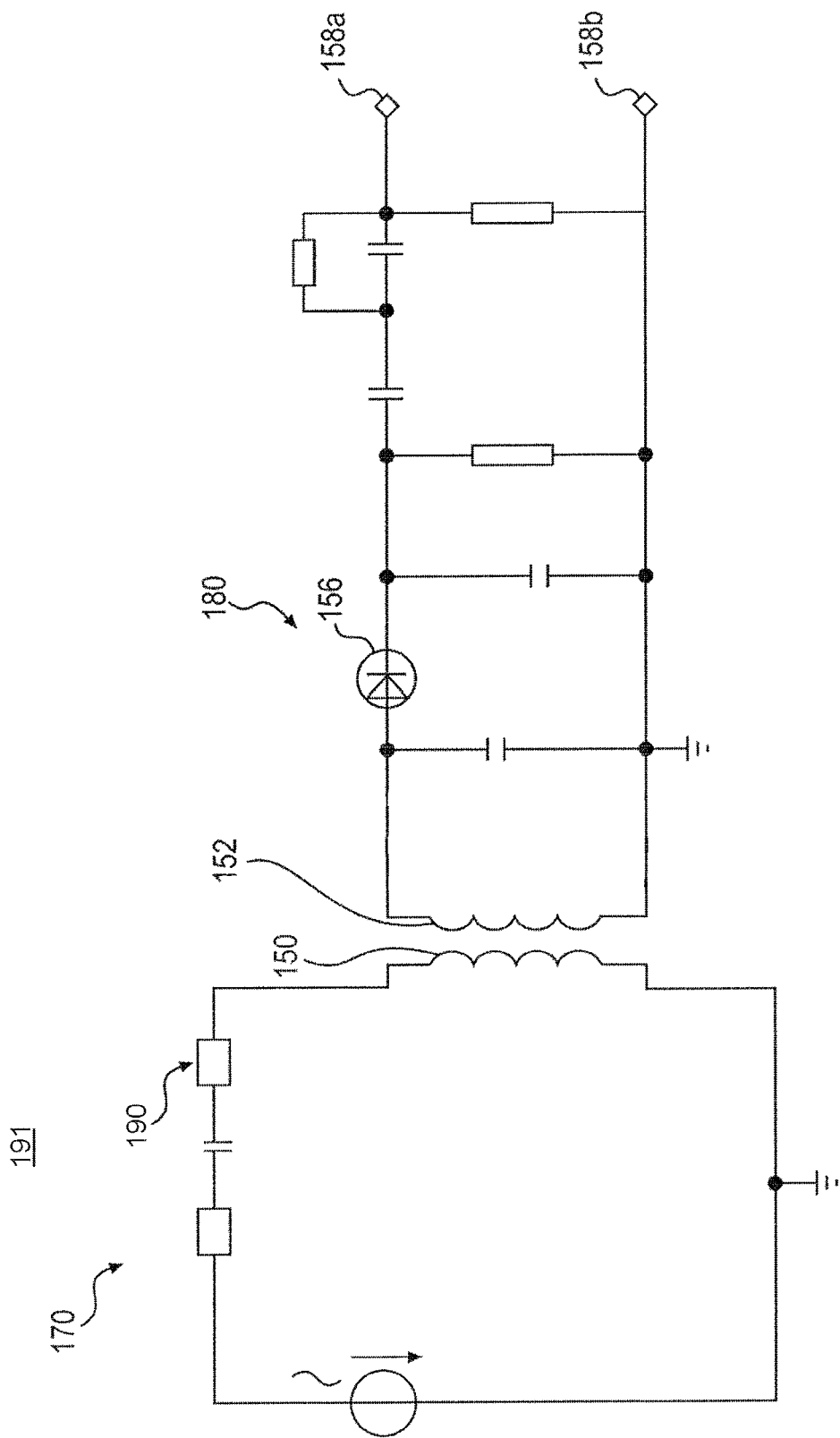
FIG. 6 illustrates circuitry of an implant unit and an external unit, according to an exemplary embodiment of the present disclosure.

FIG. 6 illustrates circuitry 170 that may be included in external unit 120 and circuitry 180 that may be included in implant unit 110. Additional, different, or fewer circuit components may be included in either or both of circuitry 170 and circuitry 180. As shown in FIG. 6, secondary antenna 152 may be arranged in electrical communication with implant electrodes 158a, 158b. In some embodiments, circuitry connecting secondary antenna 152 with implant electrodes 158a and 158b may cause a voltage potential across implant electrodes 158a and 158b in the presence of a secondary signal on secondary antenna 152. This voltage potential may be referred to as a field inducing signal, as this voltage potential may generate an electric field between implant electrodes 158a and 158b. More broadly, the field inducing signal may include any signal (e.g., voltage potential) applied to electrodes associated with the implant unit that may result in an electric field being generated between the electrodes.

Energy transfer between primary antenna 150 and secondary antenna 152 via the primary signal may be improved when a resonant frequency of primary antenna 150 and its associated circuitry 170 matches that of secondary antenna 152 and its associated circuitry 180. As used herein a resonant frequency match between two antennas may be characterized by the proximity of two resonant frequencies to one another. For example, a resonant frequency match may be considered to occur when two resonant frequencies are within 30%, 20%, 10%, 5%, 3%, 1%, 0.5%, 0.1%, or less of each other. Accordingly, a resonant frequency mismatch may be considered to occur when two resonant frequencies do not match. The proximity of the two resonant frequencies required to be considered a match may depend on the circumstances of energy transfer between the two antennas. A resonant frequency match between two antennas may also be characterized by the efficiency of energy transfer between the antennas. The efficiency of energy transfer between two antennas may depend on several factors, one of which may be the degree to which the resonant frequencies of the antennas match. Thus, if all other factors are held constant, changing the resonant frequency of one antenna with respect to the other will alter the efficiency of energy transfer. A resonant frequency match between two antennas may be considered to occur when the efficiency of energy transfer is within 50% or greater of a maximum energy transfer when all other factors remain constant. In some embodiments, a resonant frequency match may require energy transfer efficiencies of 60%, 70%, 80%, 90%, 95% or greater.

Several embodiments are provided in order to appropriately match resonant frequencies between a primary signal and a secondary antenna 152. Because the secondary antenna 152 is intended for implantation with implant unit 110, it may be difficult to adjust the resonant frequency of the antenna during use. Furthermore, due to the possibility of moisture incursion into a primary capsule encapsulating implant unit 110, implant circuitry 180, and secondary antenna 152, a resonant frequency of the implant unit 110 may drift after implantation. Other factors present during implantation may also influence the frequency drift of implant unit 110 after implantation. This drifting of the resonant frequency may last for several days to several months after implantation before stabilizing. For example, the resonant frequency of an implant unit 110 may drift from 8.1 kHz to 7.9 kHz. Through experimentation or simulation, it may be possible to predict by how much the resonant frequency may drift. Thus, using the example above, if a long term resonant frequency value of 7.9 kHz is desired, an implant unit 110 may be manufactured with a resonant frequency value of 8.1 kHz prior to implantation.

Resonant frequency values of manufactured implant units 110 may be adjusted during the manufacturing process through the use of at least one trimming capacitor. In one embodiment, a carrier 161 may be manufactured with all or some of the components of the final implant unit, including, for example, secondary antenna 152, implant circuitry 180, modulation electrodes 158a, 158b. The resonant frequency of this assembly may then be measured or otherwise determined. Due to variations in manufacturing processes and materials, the resonant frequency of each manufactured unit may differ. Thus, in order to meet a specific resonance frequency, each implant unit may be adjusted through the addition of one or more trimming capacitors to the implant circuitry 180 prior to encapsulation. In one embodiment, a capacitor may be laser trimmed to a predetermined capacitance value before insertion into implant circuitry 180. In another embodiment, a stock capacitor of known value may be inserted into implant circuitry 180. In still another embodiment, a plurality of capacitors may be inserted into implanted circuitry 180 to appropriately adjust the resonant frequency of implant unit 110. Such a plurality of capacitors may include a series of capacitors having progressively smaller capacitance values, and a resonant frequency of the assembly may be measured after the insertion of each capacitor prior to choosing and inserting the next. In this fashion, implantable circuit 180 may include at least one capacitor configured to create a predetermined mismatch between a resonant frequency of implantable circuit 180 and external circuit 170.

In addition to resonant frequency drift in implant unit 110, a resonant frequency of primary antenna 152 may vary temporally due, for example, to changing environmental conditions. For example, the application of the antenna 152 to the skin of a subject may cause bending of the primary antenna 152 to conform to the skin of a subject. Such bending may cause a shift in the spatial relationship among coils within primary antenna 152, which may lead to a change in resonant frequency. Other factors associated, e.g., with the condition of the subject's skin (e.g., moisture, sweat, oil, hair, etc.) may also change over time and may contribute to a change in resonant frequency of the primary antenna 152. The temporal variance in resonant frequency of primary antenna may be between 0-5%, up to 10%, or up to 20% or more. Thus, a current resonant frequency of the primary antenna 152 (e.g., a resonant frequency exhibited by the primary antenna or a circuit including the primary antenna at a particular point in time or over a time duration) may be adjusted to counter effects of changing environmental conditions as well as to match frequencies with a resonant frequency of an implantable circuit 180.

Processor 144 of the external unit may be configured to determine a resonant frequency mismatch between an external circuit 170 associated with primary antenna 152 and an implantable circuit 180 associated with secondary antenna 150 and adjust a resonant frequency of the external circuit 170 associated with primary antenna 152 in order to reduce or eliminate the resonant frequency mismatch. During transmission of a primary signal from a primary antenna to a secondary antenna, processor 144 may be configured to determine a resonant frequency mismatch based on a primary coupled signal component present on the primary antenna due coupling between primary antenna 152 and secondary antenna 150. Monitoring a primary coupled signal component by the processor 144 may provide an indication of transmission efficiency, which may in turn be an indication of resonant frequency mismatch. The primary coupled signal component and the interaction between primary antenna 152 and secondary antenna 150 are explained in greater detail below.

Upon determining a resonant frequency mismatch between an external circuit 170 associated with primary antenna 152 and an implantable circuit 180 associated with secondary antenna 150, processor 144 may adjust the resonant frequency of the external circuit 170 to reduce the mismatch. A resonance matching unit 190 may be in electrical communication with the external circuit 170 to facilitate the alteration of the resonant frequency of the external circuit 170. The circuit formed between the external circuit 170 and the resonance matching unit 190 may include an adjustable resonance circuit 191. Such alteration may be performed, for example, through the selective inclusion or exclusion of at least one capacitor into or out of the adjustable resonance circuit 191 formed between the external circuit 170 and the resonance matching unit 190. Adding (or subtracting) capacitors in resonance matching unit 190 may cause a change in the resonant frequency of the adjustable resonance circuit 191. Resonance matching unit 190 may be provided with one or more trim capacitors configured, through processor 144 controlled switches, for selective inclusion and exclusion. The switches may include, for example, transistors or relays. Thus, processor 144 may include or exclude a capacitor adjustable resonance circuit 191 by opening or closing a switch associated with the respective capacitor. Providing a single capacitor, therefore, permits processor 144 to switch the resonant frequency of the adjustable resonance circuit 191 between two different values. In an exemplary embodiment, a bank of six capacitors may be provided, permitting processor 144 to switch the resonant frequency of the adjustable resonance circuit 191 between 64 (i.e., $2^6$) different values. In alternative embodiments, more or fewer capacitors may be provided for adjusting the resonant frequency of the adjustable resonance circuit 191 to reduce the mismatch.

In an exemplary embodiment, processor 144 may be configured to switch capacitors from a capacitor bank into and out of the adjustable resonance circuit 191 during transmission of a primary signal to determine a capacitor combination that changes (e.g., increases) transmission efficiency and resonant frequency match. In some embodiments, processor 144 may be configured to select an optimal combination of capacitors to provide a best resonant frequency match. In some embodiments, processor 144 may be configured to select an optimal combination of capacitors, based on a detected magnitude of the power transmitted to the implant unit. In alternative embodiments, processor 144 may be configured to select a combination of capacitors that provides a resonant frequency match surpassing a predetermined threshold, regardless of whether such combination produces an optimal resonant frequency match.

Resonant frequency matching between a primary antenna 150 and a secondary antenna 152 may increase the efficiency of energy transfer between the antennas. In additional embodiments, external unit 120 may be provided with features that may facilitate development of a match between a frequency of a primary signal and a resonant frequency of the external circuit 170 associated with primary antenna 150. Development of such a match may further increase the efficiency of external unit 120. Some conventional amplifiers may be configured to generate a signal at a single frequency. Using such an amplifier may create a mismatch between the signal generated by the amplifier and the resonant frequency of the adjustable resonance circuit 191 when the adjustable resonance circuit 191 is adjusted to match frequencies with an implant unit 110. Thus, in some embodiments, self-resonant circuits may be provided for use with a resonance matching unit 190, as further described below with respect to FIGS. 7 and 8.

Figure 7:
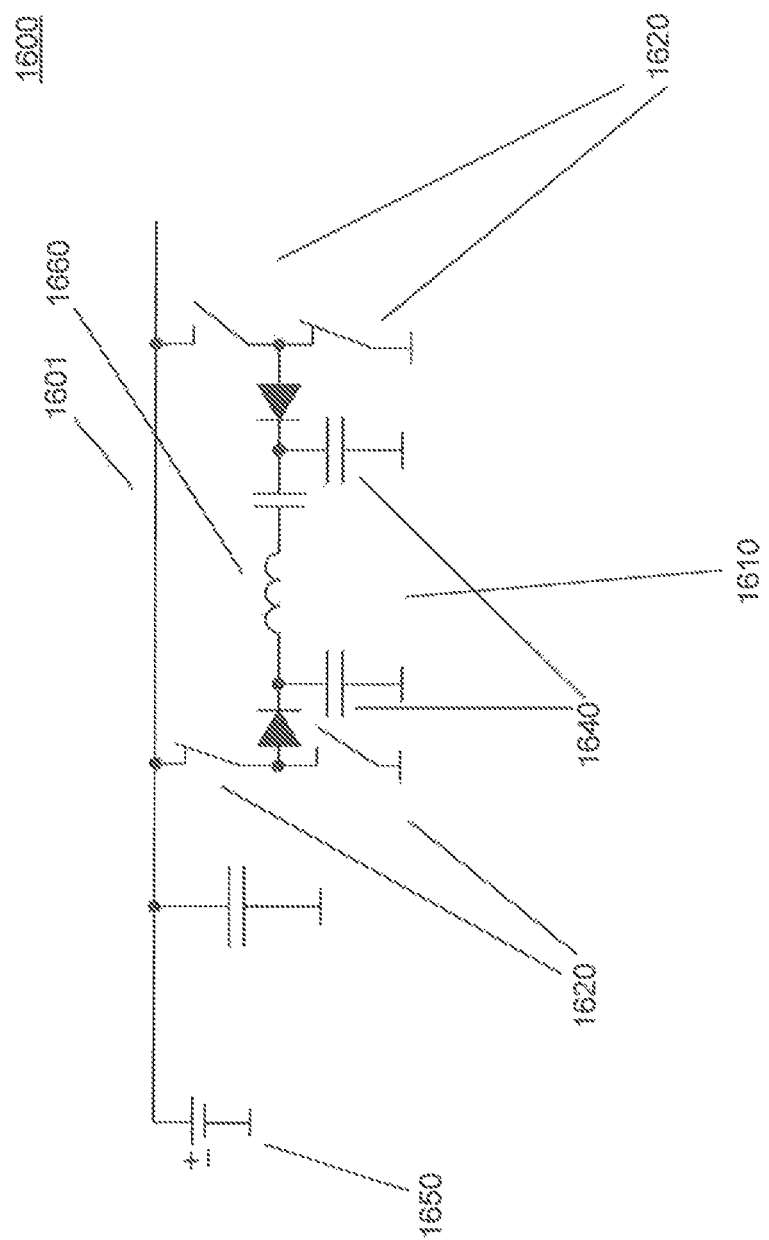
FIG. 7 depicts a self-resonant transmitter employing a modified class D amplifier.

FIG. 7 depicts an embodiment illustrating a self-resonant transmitter circuit employing a modified class D amplifier for use with resonant frequency matching methods. Modified class D amplifier 1600 may be used in place of, or in addition to, any or all of the elements of external unit 120 depicted in FIG. 3. For example, modified class D amplifier 1600 may replace signal source 142 and amplifier 146. In this embodiment, processor 144 may be configured to adjust the operation of a class D amplifier to provide a frequency match between a generated signal and a resonant frequency of an adjustable resonance circuit 191. Because the resonant frequency adjustable resonance circuit 191 may be adjusted to match that of implanted circuit 180 associated with secondary antenna 152 during operation, it may be beneficial to adjust the frequency of the generated signal as well to improve efficiency within the adjustable resonance circuit 191 external unit 120. Modified class D amplifier 1600 may be used to provide such an adjustment as follows. Modified class D amplifier 1600 includes an H bridge 1601 including switches (such as MOSFETs) 1620. Between the switches, an adjustable resonance transmitter circuit 1610 may be provided. Power to the modified class D amplifier may be provided by supply 1650, which may include a battery, for example. Adjustable resonance transmitter circuit 1610 may include adjustable resonance circuit 191. Thus, adjustable resonance transmitter circuit 1610 may include at least a primary antenna 150 and a resonance matching unit 190. FIG. 7 illustrates an exemplary self-resonant transmitter circuit 1610, depicting multiple capacitances 1640 and inductances 1660. In some embodiments, resonance matching unit 190 may take the place of some or all of capicitances 1640. In some embodiments, adjustable resonance transmitter circuit 1610 may include a primary antenna 150, and thus inductance 1660 may include the inductance of antenna 150. Capacitances 1640 may include multiple capacitors, combinations of which may be chosen from among trim capacitors as described above, in order to selectively provide an appropriate value of capacitance 1640. The value of capacitance 1640 may be selected for resonant frequency matching to adjustable resonance circuit 191. Inductances 1660 may be provided at least partially by primary antenna 150. Processor 144 may also adjust a driving frequency of the H bridge switches 1620 in order to generate a signal of a frequency that matches the resonant frequency of self-resonant circuit 1610. By selectively opening and closing switches 1620 appropriately, the DC voltage signal of supply 1650 may be converted into a square wave of a selected frequency. This frequency may be selected to match the resonant frequency of adjustable resonance circuit 1610 in order to change (e.g., increase) the efficiency of the circuit.

Figure 8:
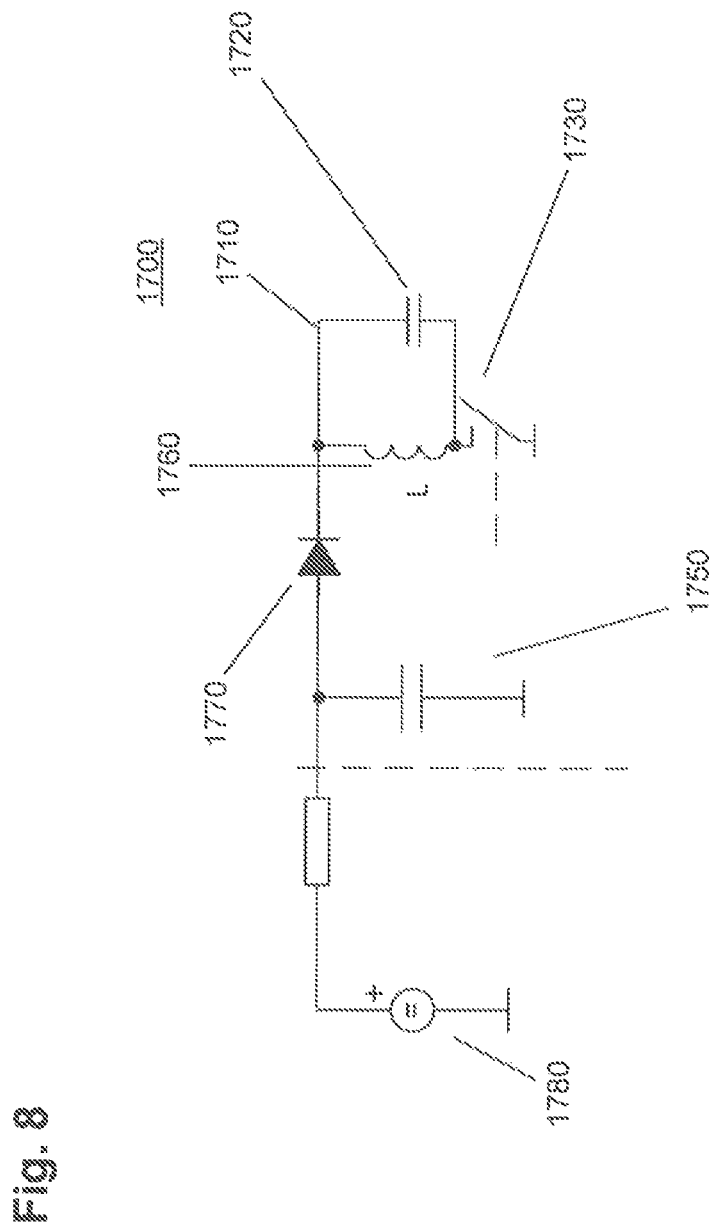
FIG. 8 depicts a pulsed mode self-resonant transmitter.

FIG. 8 depicts an additional embodiment illustrating a pulsed mode self-resonant transmitter 1700 for use with resonant frequency matching methods. Pulsed mode self-resonant transmitter 1700 may be used in place of, or in addition to, any or all of the elements of external unit 120 depicted in FIG. 3. For example, pulsed mode self-resonant transmitter 1700 may replace signal source 142 and amplifier 146. In this embodiment, processor 144 may be configured to control the circuit through a power release unit, depicted in the present embodiment as switch 1730. A power release unit may include a transistor, relay, or similar switching device. Pulsed mode self-resonant transmitter 1700 may include a primary power source 1780, for example, a battery or alternative source of power. Transmitter 1700 may include a power storage unit, such as storage capacitor 1750. Other suitable power storage units may also be utilized, such as an inductor and/or battery, as well as combinations of these storage elements. Transmitter 1700 may also include a self-resonant transmitter circuit 1710, including resonance capacitance 1720 and a resonance inductance 1760. Resonance inductance 1760 may be provided at least partially by primary antenna 150.

Transmitter 1700 may operate in the following manner, among others. Processor 144 may be configured to control the power release unit, illustrated in FIG. 8 as switch 1730. Processor 144 may be configured to control a mode of operation of the power release unit such that in a first mode of operation the power storage unit receives power from the power source, and in a second mode of operation, the power storage unit releases power to the antenna to cause an oscillation in the primary antenna at a resonance frequency.

For example, in a first mode of operation, the power storage unit, for example, storage capacitor 1750, may be configured to store energy from power source 1780. When switch 1730 is maintained in an open position, or a first state, current from power source 1780 may flow into storage capacitor 1750 which thereby stores energy by accumulating electrical charge.

The power release unit may be configured to cause the release a pulse of energy from the power storage unit to primary antenna 150 after the power storage unit has accumulated certain amount electrical charge. In a second mode of operation, when switch 1730 is closed, or moved to a second state, charged storage in capacitor 1750 drives current into the self-resonant circuit 1710 during a current loading period, where energy is stored in inductance 1760. Due to the operation of diode 1770, current flow into circuit 1710 will be cut off after a period of energy accumulation. The current transferred to circuit 1710 will then oscillate freely within circuit 1710 at the resonant frequency of circuit 1710 and thus generate a signal for transmission to the implant through primary antenna 150 (which is included in the circuit and creates at least a portion of inductance 1760). During this free oscillation period, the amplitude of the oscillations may diminish at a rate determined by the components of circuit 1710. When the oscillations have diminished to a desired level, for example, to between 5% and 10%, between 10% and 50%, or between 50% and 90% of an initial amplitude, switch 1730 may be closed again to permit storage capacitor 1750 to enter a current loading period again. During the free oscillation period, oscillation amplitude may be measured, for example, by processor 144 to determine the appropriate operation of switch 1730. In some embodiments, a current loading period may be between 0.5 and 10 μs, or between 2 and 5 μs. In some embodiments, a free oscillation period may be between 10 and 30 μs. Switch 1730 may be opened and closed several times in order to maintain a desired level of current flow in circuit 1710 for a desired period of time by assembling a series of current loading period and free oscillation periods. The desired period of time may correspond to a sub-pulse of a stimulation control signal, discussed in greater detail below. The operation of switch 1730 may be adjusted by processor 144 to increase the efficacy of modulation signals generated in implant unit 110. Such adjustments may be based, for example, on feedback received from implant unit 110, as discussed herein.

Storage capacitor 1750 may be selected to store enough energy for a complete stimulation sub-pulse, which may be, for example, between 50 and 250 μs, or between 1 μs and 2 ms. After delivery of a stimulation sub-pulse, switch 1730 may be closed again in order to permit storage capacitor 1750 to accumulate energy from power source 1780. Such accumulation may occur, for example, over a time period of between 5 and 50 milliseconds. Energy accumulated over this accumulation period may be, for example, between 1 microjoule and 10 millijoules.

Storage capacitor 1750 may be selected so as to have characteristics permitting the current in circuit 1710 to rise to a desired level at a desired rate. In some embodiments, the capacitor 1750 may be selected such that the current in circuit 1710 may change rapidly to permit a corresponding rapid increase in transmission power. For example, capacitor 1750 may be selected so as to permit the current in circuit 1710 to rise to a desired value, (e.g. between 100 mAmps and 1 Amp) during the current loading period. In some embodiments, capacitor 1750 may be selected such that a maximum value of current in circuit 1710 is higher than may be possible using power source 1780 alone. For example, capacitor 1750 may be selected so as to drive a current in circuit 1710 that is 5, 10, 20, or 100 times greater than may be permitted through the use of power source 1780 alone. For example, by utilizing the pulsed mode resonant transmitter, a battery having a voltage between 3 and 6 volts used as power source 1780 may yield a voltage in circuit 1710 of between 300 and 600 volts. Suitable capacitors may be chosen in the range of 1 microfarad to 100 microfarads.

Circuit 1710 may be configured so as to permit a power storage unit to release a desired portion of its stored energy in a desired time period—i.e. the current loading period as described above. For example, circuit 1710 may be configured to permit a power storage unit, such as storage capacitor 1750 to release between 1% and 10% of its accumulated charge in a time period between 1 and 10 microseconds.

Because the signal for transmission is generated by the self resonance of circuit 1710, it has a frequency dictated by the resonant frequency of circuit 1710. Such an arrangement may offer more efficient transmission than configurations that drive a transmission circuit with a signal that does not match the resonant frequency of the transmission circuit. Generating a transmission signal in the manner described may minimize the risk of reductions in energy transfer efficiency caused by changes in resonance of the transmission circuit. As discussed above, such temporal resonance changes in the transmission circuit may range between 0-5%, up to 10%, up to 20% or more.

Components of transmitter 1700 may be chosen such that the current loading period is approximately two microseconds, and a period of free oscillation in circuit 1710 is between 10 and 20 microseconds. Other components may be selected, however, to provide any desired current loading period or free oscillation period. As described elsewhere in this disclosure, stimulation pulses of varying lengths may be desired. Stimulation pulses of longer than a single period of free oscillation may be constructed by multiple cycles of loading and releasing energy from storage capacitor 1750 into circuit 1710. Storage capacitor 1750 may itself be chosen to store enough charge to drive a large number of oscillation cycles (e.g. between 10 and 100) in order to construct entire stimulation pulses without requiring recharging from power source 1780.

In some embodiments, transmitter 1700 may be used in conjunction with resonance matching unit 190. As discussed above, due to changes in environmental conditions, a resonant frequency of circuit 1710 may vary. Processor 144 may be configured to cause delivery of an impulse of energy to circuit 1710, for example, via operation of a power release unit such as switch 1730. This impulse of energy may excite circuit 1710 and cause oscillations in circuit 1710 at the current resonant frequency of the external circuit such that power is delivered from primary antenna 150 to implant unit 110 at the current resonant frequency of the circuit 1710. Resonance matching unit 190 may be in electrical communication (e.g., direct or indirect electrical connection) with circuit 1710, and may be configured, under control of processor 144, to alter the current resonant frequency of the circuit formed by circuit 1710 and matching unit 190. Such alterations of the current resonant frequency may be performed, for example, to optimize transmission efficiency with implant unit 121.

Pulsed mode self-resonant transmitter 1700 may provide several advantages. As described above, because the transmission signal is generated by the self-resonance of circuit 1710, it likely will match the resonant frequency of circuit 1710, obviating a need to match the frequency of the generated signal with the circuit resonance frequency. Further, because energy is stored in capacitor 1750 prior to discharge into circuit 1710, a greater flexibility in choice of power source 1780 may be provided. Effective neural modulation by an implant unit may depend on current levels that rise rapidly.

Naturally functioning neurons function by transmitting action potentials along their length. Structurally, neurons include multiple ion channels along their length that serve to maintain a voltage potential gradient across a plasma membrane between the interior and exterior of the neuron. Ion channels operate by maintaining an appropriate balance between positively charged sodium ions on one side of the plasma membrane and negatively charged potassium ions on the other side of the plasma membrane. A sufficiently high voltage potential difference created near an ion channel may exceed a membrane threshold potential of the ion channel. The ion channel may then be induced to activate, pumping the sodium and potassium ions across the plasma membrane to switch places in the vicinity of the activated ion channel. This, in turn, further alters the potential difference in the vicinity of the ion channel, which may serve to activate a neighboring ion channel. The cascading activation of adjacent ion channels may serve to propagate an action potential along the length of the neuron. Further, the activation of an ion channel in an individual neuron may induce the activation of ion channels in neighboring neurons that, bundled together, form nerve tissue. The activation of a single ion channel in a single neuron, however, may not be sufficient to induce the cascading activation of neighboring ion channels necessary to permit the propagation of an action potential. Thus, the more ion channels in a locality that may be recruited by an initial potential difference, caused through natural means such as the action of nerve endings or through artificial means, such as the application of electric fields, the more likely the propagation of an action potential may be. The process of artificially inducing the propagation of action potentials along the length of a nerve may be referred to as stimulation, or up modulation.

Neurons may also be prevented from functioning naturally through constant or substantially constant application of a voltage potential difference. After activation, each ion channel experiences a refractory period, during which it "resets" the sodium and potassium concentrations across the plasma membrane back to an initial state. Resetting the sodium and potassium concentrations causes the membrane threshold potential to return to an initial state. Until the ion channel restores an appropriate concentration of sodium and potassium across the plasma membrane, the membrane threshold potential will remain elevated, thus requiring a higher voltage potential to cause activation of the ion channel. If the membrane threshold potential is maintained at a high enough level, action potentials propagated by neighboring ion channels may not create a large enough voltage potential difference to surpass the membrane threshold potential and activate the ion channel. Thus, by maintaining a sufficient voltage potential difference in the vicinity of a particular ion channel, that ion channel may serve to block further signal transmission.

The membrane threshold potential may also be raised without eliciting an initial activation of the ion channel. If an ion channel (or a plurality of ion channels) are subjected to an elevated voltage potential difference that is not high enough to surpass the membrane threshold potential, it may serve to raise the membrane threshold potential over time, thus having a similar effect to an ion channel that has not been permitted to properly restore ion concentrations. Thus, an ion channel may be recruited as a block without actually causing an initial action potential to propagate. This method may be valuable, for example, in pain management, where the propagation of pain signals is undesired. As described above with respect to stimulation, the larger the number of ion channels in a locality that may be recruited to serve as blocks, the more likely the chance that an action potential propagating along the length of the nerve will be blocked by the recruited ion channels, rather than traveling through neighboring, unblocked channels.

Slowly rising current levels in a modulation signal may affect a nerve in a similar fashion. That is, a current level (and thus voltage potential difference) that increases slowly may serve to raise the membrane threshold potential during the application of the modulation signal, thus causing the nerve to require a higher ultimate current level to achieve modulation, which may result in diminished or absent modulation. Applying a modulation signal such that the current level (or power level) of the signal increases rapidly or greater than a threshold rate may not give the nerve time to react, and thus may ultimately produce more effective modulation at lower current levels. In contrast, using a slow current ramp or a rate lower than a threshold rate may ultimately require higher levels of current to achieve effective neuromodulation. Thus, in order to operate in certain modes, the power transferred to implant unit 110 may be required to increase at a rate that surpasses a power increase threshold rate. To achieve this with a battery alone may require a high-voltage and/or high-current battery. Such a battery may be expensive and/or difficult to design. This need may be obviated by transmitter 1700, which permits the delivery of a rapidly changing current levels and high peak current levels through the use of a power source incapable of delivering the threshold rate of power increase, such as a relatively low voltage/low current battery.

In some embodiments, a threshold rate of power increase in the implant may include an increase in current flow through the implant from substantially zero current to a current level sufficient for effective modulation (e.g., a current between 200 μAmps and 3 mAmps) in less than 20 microseconds, less than 10 microseconds, or less than 5 microseconds. Thus, for example, a threshold rate of power increase may include a current increase between 0.01-0.6 milliamps per microsecond. In some embodiments, a threshold rate of power increase may include a current increase between 0.05-0.2 milliamps per microsecond.

Transmitter 1700 may also offer enhanced efficiency. Transmitter 1700 also may use fewer switches (e.g. transistors) than does a conventional amplifying circuit. Each switch may be a source of energy loss, contributing to an overall less efficient circuit. The presence of a single switch 1730 in transmitter 1700 may increase the efficiency of the circuit as a whole.

The field inducing signal may be generated as a result of conditioning of the secondary signal by circuitry 180. As shown in FIG. 6, circuitry 170 of external unit 120 may be configured to generate an AC primary signal on primary antenna 150 that may cause an AC secondary signal on secondary antenna 152. In certain embodiments, however, it may be advantageous (e.g., in order to generate a unidirectional electric field for modulation of a nerve) to provide a DC field inducing signal at implant electrodes 158a and 158b. To convert the AC secondary signal on secondary antenna 152 to a DC field inducing signal, circuitry 180 in implant unit 110 may include an AC-DC converter. The AC to DC converter may include any suitable converter known to those skilled in the art. For example, in some embodiments the AC-DC converter may include rectification circuit components including, for example, diode 156 and appropriate capacitors and resistors. In alternative embodiments, implant unit 110 may include an AC-AC converter, or no converter, in order to provide an AC field inducing signal at implant electrodes 158a and 158b.

As noted above, the field inducing signal may be configured to generate an electric field between implant electrodes 158a and 158b. In some instances, the magnitude and/or duration of the generated electric field resulting from the field inducing signal may be sufficient to modulate one or more nerves in the vicinity of electrodes 158a and 158b. In such cases, the field inducing signal may be referred to as a modulation signal. In other instances, the magnitude and/or duration of the field inducing signal may generate an electric field that does not result in nerve modulation. In such cases, the field inducing signal may be referred to as a sub-modulation signal.

Various types of field inducing signals may constitute modulation signals. For example, in some embodiments, a modulation signal may include a moderate amplitude and moderate duration, while in other embodiments, a modulation signal may include a higher amplitude and a shorter duration. Various amplitudes and/or durations of field-inducing signals across electrodes 158a, 158b may result in modulation signals, and whether a field-inducing signal rises to the level of a modulation signal can depend on many factors (e.g., distance from a particular nerve to be stimulated; whether the nerve is branched; orientation of the induced electric field with respect to the nerve; type of tissue present between the electrodes and the nerve; etc.).

Whether a field inducing signal constitutes a modulation signal (resulting in an electric field that may cause nerve modulation) or a sub-modulation signal (resulting in an electric field not intended to cause nerve modulation) may ultimately be controlled by processor 144 of external unit 120. For example, in certain situations, processor 144 may determine that nerve modulation is appropriate. Under these conditions, processor 144 may cause signal source 144 and amplifier 146 to generate a modulation control signal on primary antenna 150 (i.e., a signal having a magnitude and/or duration selected such that a resulting secondary signal on secondary antenna 152 will provide a modulation signal at implant electrodes 158a and 158b).

Processor 144 may be configured to limit an amount of energy transferred from external unit 120 to implant unit 110. For example, in some embodiments, implant unit 110 may be associated with a threshold energy limit that may take into account multiple factors associated with the patient and/or the implant. For example, in some cases, certain nerves of a patient should receive no more than a predetermined maximum amount of energy to minimize the risk of damaging the nerves and/or surrounding tissue. Additionally, circuitry 180 of implant unit 110 may include components having a maximum operating voltage or power level that may contribute to a practical threshold energy limit of implant unit 110. Processor 144 may be configured to account for such limitations when setting the magnitude and/or duration of a primary signal to be applied to primary antenna 150.

In addition to determining an upper limit of power that may be delivered to implant unit 110, processor 144 may also determine a lower power threshold based, at least in part, on an efficacy of the delivered power. The lower power threshold may be computed based on a minimum amount of power that enables nerve modulation (e.g., signals having power levels above the lower power threshold may constitute modulation signals while signals having power levels below the lower power threshold may constitute sub-modulation signals).

A lower power threshold may also be measured or provided in alternative ways. For example, appropriate circuitry or sensors in the implant unit 110 may measure a lower power threshold. A lower power threshold may be computed or sensed by an additional external device, and subsequently programmed into processor 144, or programmed into implant unit 110. Alternatively, implant unit 110 may be constructed with circuitry 180 specifically chosen to generate signals at the electrodes of at least the lower power threshold. In still another embodiment, an antenna of external unit 120 may be adjusted to accommodate or produce a signal corresponding to a specific lower power threshold. The lower power threshold may vary from patient to patient, and may take into account multiple factors, such as, for example, modulation characteristics of a particular patient's nerve fibers, a distance between implant unit 110 and external unit 120 after implantation, and the size and configuration of implant unit components (e.g., antenna and implant electrodes), etc.

Processor 144 may also be configured to cause application of sub-modulation control signals to primary antenna 150.

Such sub-modulation control signals may include an amplitude and/or duration that result in a sub-modulation signal at electrodes 158a, 158b. While such sub-modulation control signals may not result in nerve modulation, such sub-modulation control signals may enable feedback-based control of the nerve modulation system. That is, in some embodiments, processor 144 may be configured to cause application of a sub-modulation control signal to primary antenna 150. This signal may induce a secondary signal on secondary antenna 152, which, in turn, induces a primary coupled signal component on primary antenna 150.

To analyze the primary coupled signal component induced on primary antenna 150, external unit 120 may include a feedback circuit 148 (e.g., a signal analyzer or detector, etc.), which may be placed in direct or indirect communication with primary antenna 150 and processor 144. Sub-modulation control signals may be applied to primary antenna 150 at any desired periodicity. In some embodiments, the sub-modulation control signals may be applied to primary antenna 150 at a rate of one every five seconds (or longer). In other embodiments, the sub-modulation control signals may be applied more frequently (e.g., once every two seconds, once per second, once per millisecond, once per nanosecond, or multiple times per second). Further, it should be noted that feedback may also be received upon application of modulation control signals to primary antenna 150 (i.e., those that result in nerve modulation), as such modulation control signals may also result in generation of a primary coupled signal component on primary antenna 150.

The primary coupled signal component may be fed to processor 144 by feedback circuit 148 and may be used as a basis for determining a degree of coupling between primary antenna 150 and secondary antenna 152. The degree of coupling may enable determination of the efficacy of the energy transfer between two antennas. Processor 144 may also use the determined degree of coupling in regulating delivery of power to implant unit 110.

Processor 144 may be configured with any suitable logic for determining how to regulate power transfer to implant unit 110 based on the determined degree of coupling. For example, where the primary coupled signal component indicates that a degree of coupling has changed from a baseline coupling level, processor 144 may determine that secondary antenna 152 has moved with respect to primary antenna 150 (either in coaxial offset, lateral offset, or angular offset, or any combination). Such movement, for example, may be associated with a movement of the implant unit 110, and the tissue that it is associated with based on its implant location. Thus, in such situations, processor 144 may determine that modulation of a nerve in the patient's body is appropriate. More particularly, in response to an indication of a change in coupling, processor 144, in some embodiments, may cause application of a modulation control signal to primary antenna 150 in order to generate a modulation signal at implant electrodes 158a, 158b, e.g., to cause modulation of a nerve of the patient.

In an embodiment for the treatment of OSA, movement of an implant unit 110 may be associated with movement of the tongue, which may indicate the onset of a sleep apnea event or a sleep apnea precursor. The onset of a sleep apnea event of sleep apnea precursor may require the stimulation of the genioglossus muscle of the patient to relieve or avert the event. Such stimulation may result in contraction of the muscle and movement of the patient's tongue away from the patient's airway.

In embodiments for the treatment of head pain, including migraines, processor 144 may be configured to generate a modulation control signal based on a signal from a user, for example, or a detected level of neural activity in a sensory neuron (e.g. the greater occipital nerve or trigeminal nerve) associated with head pain. A modulation control signal generated by the processor and applied to the primary antenna 150 may generate a modulation signal at implant electrodes 158a, 158b, e.g. to cause inhibition or blocking of a sensory nerve of the patient. Such inhibition or blocking may decrease or eliminate the sensation of pain for the patient.

In embodiments for the treatment of hypertension, processor 144 may be configured to generate a modulation control signal based on, for example, pre-programmed instructions and/or signals from an implant indicative of blood pressure. A modulation control signal generated by the processor and applied to the primary antenna 150 may generate a modulation signal at implant electrodes 158a, 158b, e.g., to cause either inhibition or stimulation of nerve of a patient, depending on the requirements. For example, a neuromodulator placed in a carotid artery or jugular artery (i.e. in the vicinity of a carotid baroreceptor), may receive a modulation control signal tailored to induce a stimulation signal at the electrodes, thereby causing the glossopharyngeal nerve associated with the carotid baroreceptors to fire at an increased rate in order to signal the brain to lower blood pressure. Similar modulation of the glossopharyngeal nerve may be achieved with a neuromodulator implanted in a subcutaneous location in a patient's neck or behind a patient's ear. A neuromodulator place in a renal artery may receive a modulation control signal tailored to cause an inhibiting or blocking signal at the electrodes, thereby inhibiting a signal to raise blood pressure carried from the renal nerves to the kidneys.

Modulation control signals may include stimulation control signals, and sub-modulation control signals may include sub-stimulation control signals. Stimulation control signals may have any amplitude, pulse duration, or frequency combination that results in a stimulation signal at electrodes 158a, 158b. In some embodiments (e.g., at a frequency of between about 6.5-13.6 MHz), stimulation control signals may include a pulse duration of greater than about 50 microseconds and/or an amplitude of approximately 0.5 amps, or between 0.1 amps and 1 amp, or between 0.05 amps and 3 amps. Sub-stimulation control signals may have a pulse duration less than about 500, or less than about 200 nanoseconds and/or an amplitude less than about 1 amp, 0.5 amps, 0.1 amps, 0.05 amps, or 0.01 amps. Of course, these values are meant to provide a general reference only, as various combinations of values higher than or lower than the exemplary guidelines provided may or may not result in nerve stimulation.

In some embodiments, stimulation control signals may include a pulse train, wherein each pulse includes a plurality of sub-pulses. An alternating current signal (e.g., at a frequency of between about 6.5-13.6 MHz) may be used to generate the pulse train, as follows. A sub-pulse may have a duration of between 50-250 microseconds, or a duration of between 1 microsecond and 2 milliseconds, during which an alternating current signal is turned on. For example, a 200 microsecond sub-pulse of a 10 MHz alternating current signal will include approximately 2000 periods. Each pulse may, in turn, have a duration of between 100 and 500 milliseconds, during which sub-pulses occur at a frequency of between 25 and 100 Hz. For example, a 200 millisecond pulse of 50 Hz sub-pulses will include approximately 10 sub-pulses. Finally, in a pulse train, each pulse may be separated from the next by a duration of between 0.2 and 2 seconds. For example, in a pulse train of 200 millisecond pulses, each separated by 1.3 seconds from the next, a new pulse will occur every 1.5 seconds. A pulse train of this embodiment may be utilized, for example, to provide ongoing stimulation during a treatment session. In the context of OSA, a treatment session may be a period of time during which a subject is asleep and in need of treatment to prevent OSA. Such a treatment session may last anywhere from about three to ten hours. In the context of other conditions to which neural modulators of the present disclosure are applied, a treatment session may be of varying length according to the duration of the treated condition.

As discussed above, a pulse train may be generated by a pulsed mode self-resonant transmitter as described herein. For example, each sub-pulse may be generated by assembling multiple current loading periods and free oscillation periods. A period between sub-pulses may include an energy accumulation period, after which another sub-pulse comprising multiple current loading periods and free oscillation periods may be generated. In this manner, a pulse train having any or all of the parameters as described above may be generated utilizing a pulsed mode self-resonant transmitter.

Processor 144 may be configured to determine a degree of coupling between primary antenna 150 and secondary antenna 152 by monitoring one or more aspects of the primary coupled signal component received through feedback circuit 148. In some embodiments, processor 144 may determine a degree of coupling between primary antenna 150 and secondary antenna 152 by monitoring a voltage level associated with the primary coupled signal component, a current level, or any other attribute that may depend on the degree of coupling between primary antenna 150 and secondary antenna 152. For example, in response to periodic sub-modulation signals applied to primary antenna 150, processor 144 may determine a baseline voltage level or current level associated with the primary coupled signal component. This baseline voltage level, for example, may be associated with a range of movement of the patient's tongue when a sleep apnea event or its precursor is not occurring, e.g. during normal breathing. As the patient's tongue moves toward a position associated with a sleep apnea event or its precursor, the coaxial, lateral, or angular offset between primary antenna 150 and secondary antenna 152 may change. As a result, the degree of coupling between primary antenna 150 and secondary antenna 152 may change, and the voltage level or current level of the primary coupled signal component on primary antenna 150 may also change. Processor 144 may be configured to recognize a sleep apnea event or its precursor when a voltage level, current level, or other electrical characteristic associated with the primary coupled signal component changes by a predetermined amount or reaches a predetermined absolute value.

Figure 9:
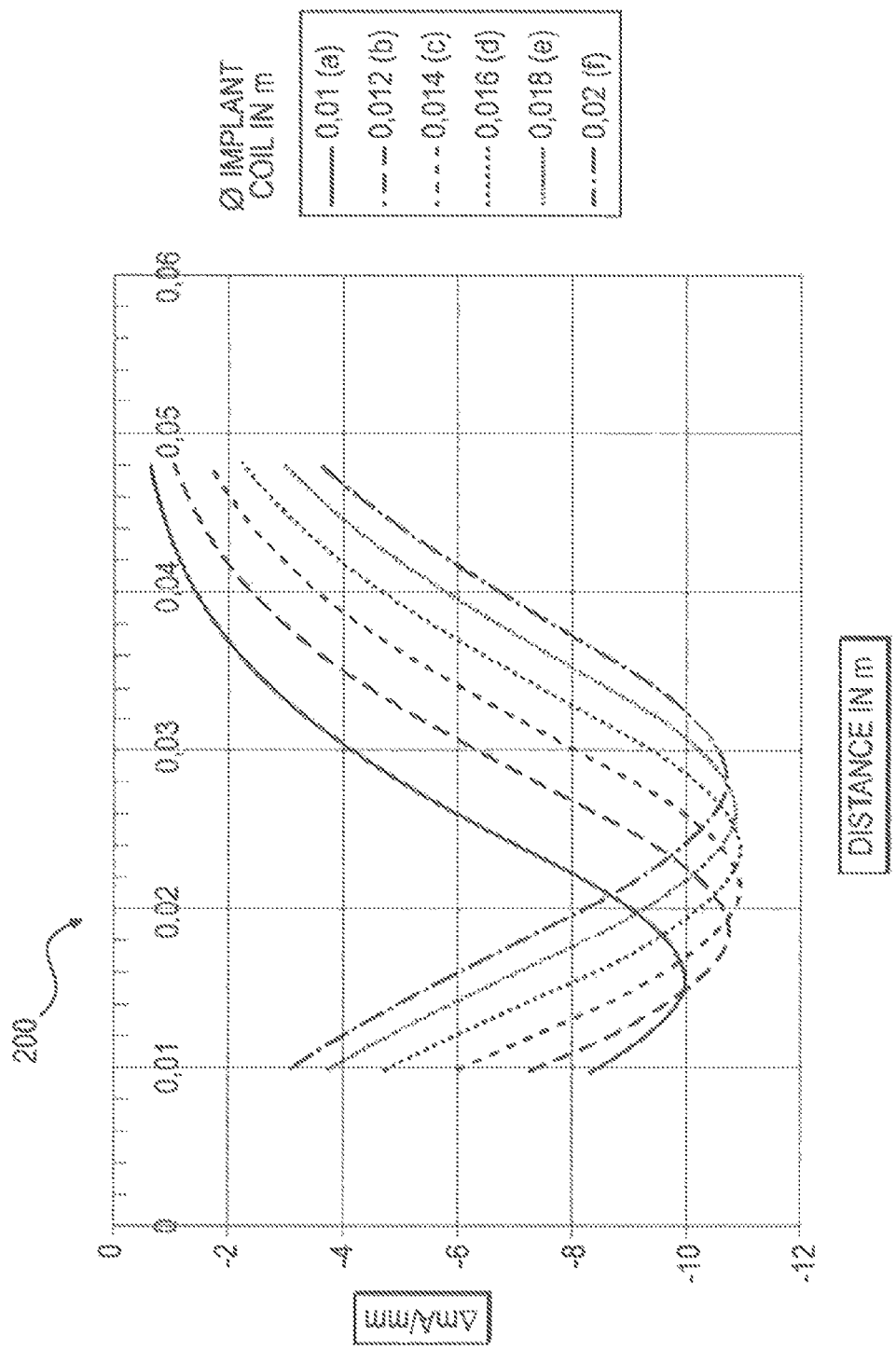
FIG. 9 illustrates a graph of quantities that may be used in determining energy delivery as a function coupling, according to an exemplary disclosed embodiment.

FIG. 9 provides a graph that illustrates this principle in more detail. For a two-coil system where one coil receives a radio frequency (RF) drive signal, graph 200 plots a rate of change in induced current in the receiving coil as a function of coaxial distance between the coils. For various coil diameters and initial displacements, graph 200 illustrates the sensitivity of the induced current to further displacement between the coils, moving them either closer together or further apart. It also indicates that, overall, the induced current in the secondary coil will decrease as the secondary coil is moved away from the primary, drive coil, i.e. the rate of change of induced current, in mA/mm, is consistently negative. The sensitivity of the induced current to further displacement between the coils varies with distance. For example, at a separation distance of 10 mm, the rate of change in current as a function of additional displacement in a 14 mm coil is approximately −6 mA/mm. If the displacement of the coils is approximately 22 mm, the rate of change in the induced current in response to additional displacement is approximately −11 mA/mm, which corresponds to a local maximum in the rate of change of the induced current. Increasing the separation distance beyond 22 mm continues to result in a decline in the induced current in the secondary coil, but the rate of change decreases. For example, at a separation distance of about 30 mm, the 14 mm coil experiences a rate of change in the induced current in response to additional displacement of about −8 mA/mm. With this type of information, processor 144 may be able to determine a particular degree of coupling between primary antenna 150 and secondary antenna 152, at any given time, by observing the magnitude and/or rate of change in the magnitude of the current associated with the primary coupled signal component on primary antenna 150.

In some embodiments, an initially detected coupling degree may establish a baseline range when the patient attaches external unit 120 to the skin. Presumably, while the patient is awake, the tongue is not blocking the patient's airway and moves with the patients breathing in a natural range, where coupling between primary antenna 150 and secondary antenna 152 may be within a baseline range. A baseline coupling range may encompass a maximum coupling between primary antenna 150 and secondary antenna 152. A baseline coupling range may also encompass a range that does not include a maximum coupling level between primary antenna 150 and secondary antenna 152. Thus, the initially determined coupling may be fairly representative of a non-sleep apnea condition and may be used by processor 144 as a baseline in determining a degree of coupling between primary antenna 150 and secondary antenna 152.

As the patient wears external unit 120, processor 144 may periodically scan over a range of primary signal amplitudes to determine current values of coupling. If a periodic scan results in determination of a degree of coupling different from the baseline coupling, processor 144 may determine that there has been a change from the baseline initial conditions.

By periodically determining a degree of coupling value, processor 144 may be configured to determine, in situ, appropriate parameter values for the modulation control signal that will ultimately result in nerve modulation. For example, by determining the degree of coupling between primary antenna 150 and secondary antenna 152, processor 144 may be configured to select characteristics of the modulation control signal (e.g., amplitude, pulse duration, frequency, etc.) that may provide a modulation signal at electrodes 158a, 158b in proportion to or otherwise related to the determined degree of coupling. In some embodiments, processor 144 may access a lookup table or other data stored in a memory correlating modulation control signal parameter values with degree of coupling. In this way, processor 144 may adjust the applied modulation control signal in response to an observed degree of coupling.

Additionally or alternatively, processor 144 may be configured to determine the degree of coupling between primary antenna 150 and secondary antenna 152 during modulation. The tongue, or other structure on or near which the implant is located, and thus implant unit 110, may move as a result of modulation. Thus, the degree of coupling may change during modulation. Processor 144 may be configured to determine the degree of coupling as it changes during modulation, in order to dynamically adjust characteristics of the modulation control signal according to the changing degree of coupling. This adjustment may permit processor 144 to cause implant unit 110 to provide an appropriate modulation signal at electrodes 158a, 158b throughout a modulation event. For example, processor 144 may alter the primary signal in accordance with the changing degree of coupling in order to maintain a constant modulation signal, or to cause the modulation signal to be reduced in a controlled manner according to patient needs.

More particularly, the response of processor 144 may be correlated to the determined degree of coupling. In situations where processor 144 determines that the degree of coupling between primary antenna 150 and secondary antenna has fallen only slightly below a predetermined coupling threshold (e.g. during snoring or during a small vibration of the tongue or other sleep apnea event precursor), processor 144 may determine that only a small response is necessary. Thus, processor 144 may select modulation control signal parameters that will result in a relatively small response (e.g., a short stimulation of a nerve, small muscle contraction, etc.). Where, however, processor 144 determines that the degree of coupling has fallen substantially below the predetermined coupling threshold (e.g., where the tongue has moved enough to cause a sleep apnea event), processor 144 may determine that a larger response is required. As a result, processor 144 may select modulation control signal parameters that will result in a larger response. In some embodiments, only enough power may be transmitted to implant unit 110 to cause the desired level of response. In other words, processor 144 may be configured to cause a metered response based on the determined degree of coupling between primary antenna 150 and secondary antenna 152. As the determined degree of coupling decreases, processor 144 may cause transfer of power in increasing amounts. Such an approach may preserve battery life in the external unit 120, may protect circuitry 170 and circuitry 180, may increase effectiveness in addressing the type of detected condition (e.g., sleep apnea, snoring, tongue movement, etc.), and may be more comfortable for the patient.

In some embodiments, processor 144 may employ an iterative process in order to select modulation control signal parameters that result in a desired response level. For example, upon determining that a modulation control signal should be generated, processor 144 may cause generation of an initial modulation control signal based on a set of predetermined parameter values. If feedback from feedback circuit 148 indicates that a nerve has been modulated (e.g. if an increase in a degree of coupling is observed), then processor 144 may return to a monitoring mode by issuing sub-modulation control signals. If, on the other hand, the feedback suggests that the intended nerve modulation did not occur as a result of the intended modulation control signal or that modulation of the nerve occurred but only partially provided the desired result (e.g. movement of the tongue only partially away from the airway), processor 144 may change one or more parameter values associated with the modulation control signal (e.g., the amplitude, pulse duration, etc.).

Where no nerve modulation occurred, processor 144 may increase one or more parameters of the modulation control signal periodically until the feedback indicates that nerve modulation has occurred. Where nerve modulation occurred, but did not produce the desired result, processor 144 may re-evaluate the degree of coupling between primary antenna 150 and secondary antenna 152 and select new parameters for the modulation control signal targeted toward achieving a desired result. For example, where stimulation of a nerve causes the tongue to move only partially away from the patient's airway, additional stimulation may be desired. Because the tongue has moved away from the airway, however, implant unit 110 may be closer to external unit 120 and, therefore, the degree of coupling may have increased. As a result, to move the tongue a remaining distance to a desired location may require transfer to implant unit 110 of a smaller amount of power than what was supplied prior to the last stimulation-induced movement of the tongue. Thus, based on a newly determined degree of coupling, processor 144 can select new parameters for the stimulation control signal aimed at moving the tongue the remaining distance to the desired location.

In one mode of operation, processor 144 may be configured to sweep over a range of parameter values until nerve modulation is achieved. For example, in circumstances where an applied sub-modulation control signal results in feedback indicating that nerve modulation is appropriate, processor 144 may use the last applied sub-modulation control signal as a starting point for generation of the modulation control signal. The amplitude and/or pulse duration (or other parameters) associated with the signal applied to primary antenna 150 may be iteratively increased by predetermined amounts and at a predetermined rate until the feedback indicates that nerve modulation has occurred.

Processor 144 may be configured to determine or derive various physiologic data based on the determined degree of coupling between primary antenna 150 and secondary antenna 152. For example, in some embodiments the degree of coupling may indicate a distance between external unit 120 and implant unit 110, which processor 144 may use to determine a position of external unit 120 or a relative position of a patient's tongue. Monitoring the degree of coupling can also provide such physiologic data as whether a patient's tongue is moving or vibrating (e.g. whether the patient is snoring), by how much the tongue is moving or vibrating, the direction of motion of the tongue, the rate of motion of the tongue, etc.

In response to any of these determined physiologic data, processor 144 may regulate delivery of power to implant unit 110 based on the determined physiologic data. For example, processor 144 may select parameters for a particular modulation control signal or series of modulation control signals for addressing a specific condition relating to the determined physiologic data. If the physiologic data indicates that the tongue is vibrating, for example, processor 144 may determine that a sleep apnea event is likely to occur and may issue a response by delivering power to implant unit 110 in an amount selected to address the particular situation. If the tongue is in a position blocking the patient's airway (or partially blocking a patient's airway), but the physiologic data indicates that the tongue is moving away from the airway, processor 144 may opt to not deliver power and wait to determine if the tongue clears on its own. Alternatively, processor 144 may deliver a small amount of power to implant unit 110 (e.g., especially where a determined rate of movement indicates that the tongue is moving slowly away from the patient's airway) to encourage the tongue to continue moving away from the patient's airway or to speed its progression away from the airway. The scenarios described are exemplary only. Processor 144 may be configured with software and/or logic enabling it to address a variety of different physiologic scenarios with particularity. In each case, processor 144 may be configured to use the physiologic data to determine an amount of power to be delivered to implant unit 110 in order to modulate nerves associated with the tongue with the appropriate amount of energy.

The disclosed embodiments may be used in conjunction with a method for regulating delivery of power to an implant unit. The method may include determining a degree of coupling between primary antenna 150 associated with external unit 120 and secondary antenna 152 associated with implant unit 110, implanted in the body of a patient. Determining the degree of coupling may be accomplished by processor 144 located external to implant unit 110 and that may be associated with external unit 120. Processor 144 may be configured to regulate delivery of power from the external unit to the implant unit based on the determined degree of coupling.

As previously discussed, the degree of coupling determination may enable the processor to further determine a location of the implant unit. The motion of the implant unit may correspond to motion of the body part where the implant unit may be attached. This may be considered physiologic data received by the processor. The processor may, accordingly, be configured to regulate delivery of power from the power source to the implant unit based on the physiologic data. In alternative embodiments, the degree of coupling determination may enable the processor to determine information pertaining to a condition of the implant unit. Such a condition may include location as well as information pertaining to an internal state of the implant unit. The processor may, according to the condition of the implant unit, be configured to regulate delivery of power from the power source to the implant unit based on the condition data.

In some embodiments, implant unit 110 may include a processor located on the implant. A processor located on implant unit 110 may perform all or some of the processes described with respect to the at least one processor associated with an external unit. For example, a processor associated with implant unit 110 may be configured to receive a control signal prompting the implant controller to turn on and cause a modulation signal to be applied to the implant electrodes for modulating a nerve. Such a processor may also be configured to monitor various sensors associated with the implant unit and to transmit this information back to and external unit. Power for the processor unit may be supplied by an onboard power source or received via transmissions from an external unit.

In other embodiments, implant unit 110 may be self-sufficient, including its own power source and a processor configured to operate the implant unit 110 with no external interaction. For example, with a suitable power source, the processor of implant unit 110 could be configured to monitor conditions in the body of a subject (via one or more sensors or other means), determining when those conditions warrant modulation of a nerve, and generate a signal to the electrodes to modulate a nerve. The power source could be regenerative based on movement or biological function; or the power sources could be periodically rechargeable from an external location, such as, for example, through induction.

Other embodiments of the present disclosure will be apparent to those skilled in the art from consideration of the specification and practice of the present disclosure.

Additional aspects of the invention are described in the following numbered paragraphs, which are part of the description of exemplary embodiments of the invention. Each numbered paragraph stands on its own as a separate embodiment of the invention.

What is claimed is:

1. A device for treating sleep apnea by powering an implant within a body of a subject from a location external to the subject, wherein the implant requires a threshold rate of power increase in order to operate in at least one stimulate a hypoglossal nerve and thereby cause contraction of a genioglossus muscle, the device comprising:
   an antenna configured for location between a neck and a chin of the subject and to wirelessly transmit energy to the implant, the antenna being part of a resonant circuit;
   a power storage unit configured to store energy from a power source incapable of delivering the threshold rate of power increase to enable the implant unit to operate in the at least one mode; and
   a power release unit configured to release a pulse of energy from the power storage unit to the antenna, the pulse of energy being sufficient to enable the implant unit to stimulate the hypoglossal nerve to cause contraction of the genioglossus muscle, and wherein the resonant circuit is configured to generate a signal for transmission to the implant by electrical oscillation in the resonant circuit at a resonant frequency of the resonant circuit when the pulse of energy is received by the resonant circuit.

2. The device of claim 1, further comprising a substrate, wherein the antenna is associated with the substrate.

3. The device of claim 2, wherein the substrate and the antenna are flexible.

4. The device of claim 1, further comprising at least one processor configured to control a mode of operation of the power release unit such that in a first mode of operation the power storage unit receives power from the power source, and in a second mode of operation, the power storage unit releases power to the antenna to cause an oscillation in the primary antenna at a resonance frequency.

5. The device of claim 1, wherein the antenna is configured to be located external to a subject's body.

6. The device of claim 1, wherein the power source is configured to generate electrical energy.

7. The device of claim 1, wherein the power storage unit is configured to store electrical energy generated by the power source.

8. The device of claim 1, wherein the power release unit is configured to control electrical energy transfer between the power source and the power storage unit and between the power storage unit and the antenna, wherein at least the antenna is part of an electrical circuit having a resonance frequency.

* * * * *